(12) United States Patent
Huang et al.

(10) Patent No.: US 9,572,760 B2
(45) Date of Patent: Feb. 21, 2017

(54) **USES OF COMPOUNDS AND MIXTURES FROM *ANTRODIA CINNAMOMEA* MYCELIA**

(71) Applicant: Simpson Biotech Co., Ltd., Taoyuan County (TW)

(72) Inventors: Kai-Wen Huang, Taipei (TW); Chia-Chin Sheu, Taoyuan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 14/520,375

(22) Filed: Oct. 22, 2014

(65) Prior Publication Data

US 2015/0110726 A1    Apr. 23, 2015

Related U.S. Application Data

(60) Provisional application No. 61/894,695, filed on Oct. 23, 2013.

(51) Int. Cl.
| | |
|---|---|
| *A61Q 19/08* | (2006.01) |
| *A61Q 19/02* | (2006.01) |
| *A61K 31/34* | (2006.01) |
| *A61K 36/07* | (2006.01) |
| *A61K 8/49* | (2006.01) |
| *A61K 8/97* | (2006.01) |

(52) U.S. Cl.
CPC ........... *A61K 8/4913* (2013.01); *A61K 8/4973* (2013.01); *A61K 8/975* (2013.01); *A61K 31/34* (2013.01); *A61K 36/07* (2013.01); *A61Q 19/02* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | | | |
|---|---|---|---|---|
| 7,109,232 B2* | 9/2006 | Hattori | ............... | C07D 207/444 514/425 |
| 2006/0251673 A1* | 11/2006 | Hwang | ................. | A23L 1/3002 424/195.15 |
| 2013/0164233 A1* | 6/2013 | Lee | ....................... | A61Q 19/02 424/62 |

OTHER PUBLICATIONS

Kawagishi, H., et al., Novel Bioactive Compound from the Sparassis crispa Mushroom, Biosci. Biotechnol. Biochem., 71 (7), 1804-1806, 2007.*

Wu et al., 1997, Antrodia camphorata ("niu-chang-chih"), new combination of a medicinal fungus in Taiwan. Bot. Bull. Acad. Sin. 38: 273-275.

Lin et al., 2007, Factors affecting mycelial biomass and exopolysacharide production in submerged cultivation of Antrodia cinnamomea using complex media. Bioresource Technology 98: 2511-2517.

Nakamura et al., 2004, Five new maleic and succinic acid derivatives from the mycelium of Antrodia comphorata and their cytotoxic effects on LLC tumor cell line. J Nat Prod 67: 46-48.

Phuong do T et al., 2009, inhibitory effects of antrodins A-E from Antrodia cinnamomea and their metabolites on hepatitis C virus protease. Phytother Res. Apr;23(4):582-4.

Han et al., Protective Effects of a Neutral Polysaccharide Isolated from the Mycelium of Antrodia cinnamomea on Propionibacterium acnes and Lipopolysaccharide Induced Hepatic Injury in Mice, Chem. Pharm. Bull. 54(4) 496-500 (2006).

* cited by examiner

*Primary Examiner* — H. Sarah Park
(74) *Attorney, Agent, or Firm* — Hannah M. Tien

(57) ABSTRACT

The present invention relates to novel uses of compounds from *Antrodia cinnamomea* mycelia and mixtures comprising the compounds. The novel uses comprise whitening skin, combating skin ageing, reducing scar formation, inducing or enhancing liver regeneration, or treating fibrosis or a fibrosis-associated disorder in a subject in need thereof. The compounds have the formula

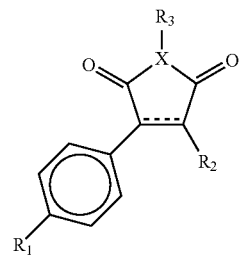

and preferably are selected from 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, and 3R*,4R*-1-hydroxy-3-isobutyl-4-[4-(3-methyl-2-butenyloxy)phenyl]pyrrolidine-2,5-dione.

7 Claims, 23 Drawing Sheets

USES OF COMPOUNDS AND MIXTURES FROM *ANTRODIA CINNAMOMEA* MYCELIA

CROSS-REFERENCES TO RELATED APPLICATIONS

The present application claims priority to U.S. Provisional Appl. No. 61/894,695, filed at Oct. 23, 2013, incorporated herein by reference in their entireties.

FIELD OF THE INVENTION

The present invention relates to uses of compounds and mixtures from *Antrodia cinnamomea* mycelia.

BACKGROUND OF THE INVENTION

The fruiting body of *Antrodia cinnamomea* T. T. Chang & W. N. Chou (a taxonomic synonym of *Antrodia camphorate*, referring to Wu et al., 1997, *Antrodia camphorate* ("niu-chang-chih"), new combination of a medicinal fungus in Taiwan. *Bot. Bull. Acad. Sin.* 38: 273-275) is a highly valued folk medicine in Taiwan. It is used as an antidote and for diarrhea, abdominal pain, hypertension, itchy skin, and liver cancer. Some bioactive constituents from the fruiting body of *Antrodia cinnamomea* have been isolated and characterized as a series of polysaccharides, steroids, triterpenoids, and sesquiterpene lactone (Lin et al., 2007, Factors affecting mycelial biomass and exopolysacharide production in submerged cultivation of *Antrodia cinnamomea* using complex media. *Bioresource Technology* 98: 2511-2517). In previous studies, five new maleic and succinic acid derivatives (Compound 1-5) are isolated from the mycelium of *Antrodia cinnamomea* (Nakamura et al., 2004, Five new maleic and succinic acid derivatives from the mycelium of *Antrodia comphorata* and their cytotoxic effects on LLC tumor cell line. *J Nat Prod* 67: 46-48).

U.S. Pat. No. 7,109,232 discloses Compounds 1-5 from *Antrodia cinnamomea* mycelia and their uses such as hepatoprotection, anti-inflammation or anti-tumor activity and preparation. The above Compounds 1-5 are further named as Antrodins A-E in another article (Phuong do T et al., 2009, inhibitory effects of antrodins A-E from *Antrodia cinnamomea* and their metabolites on hepatitis C virus protease. *Phytother Res.* April; 23(4):582-4). According to the prior arts, it is noted that these Compounds 1-5 from *Antrodia cinnamomea* mycelia not only have similar structures but also have similar activities.

BRIEF DESCRIPTION OF THE DRAWINGS

FIG. 4A shows that the gene expression of anti-oxidant enzyme including CuZnSOD, MnSOD, Catalase and Glutathione peroxidase were up-regulated prominently, especially in the animals fed with 320 mg/kg/day. FIG. 4B shows that the gene expression of NADPH oxidase was down-regulated.

SUMMARY OF THE INVENTION

Figure 1:
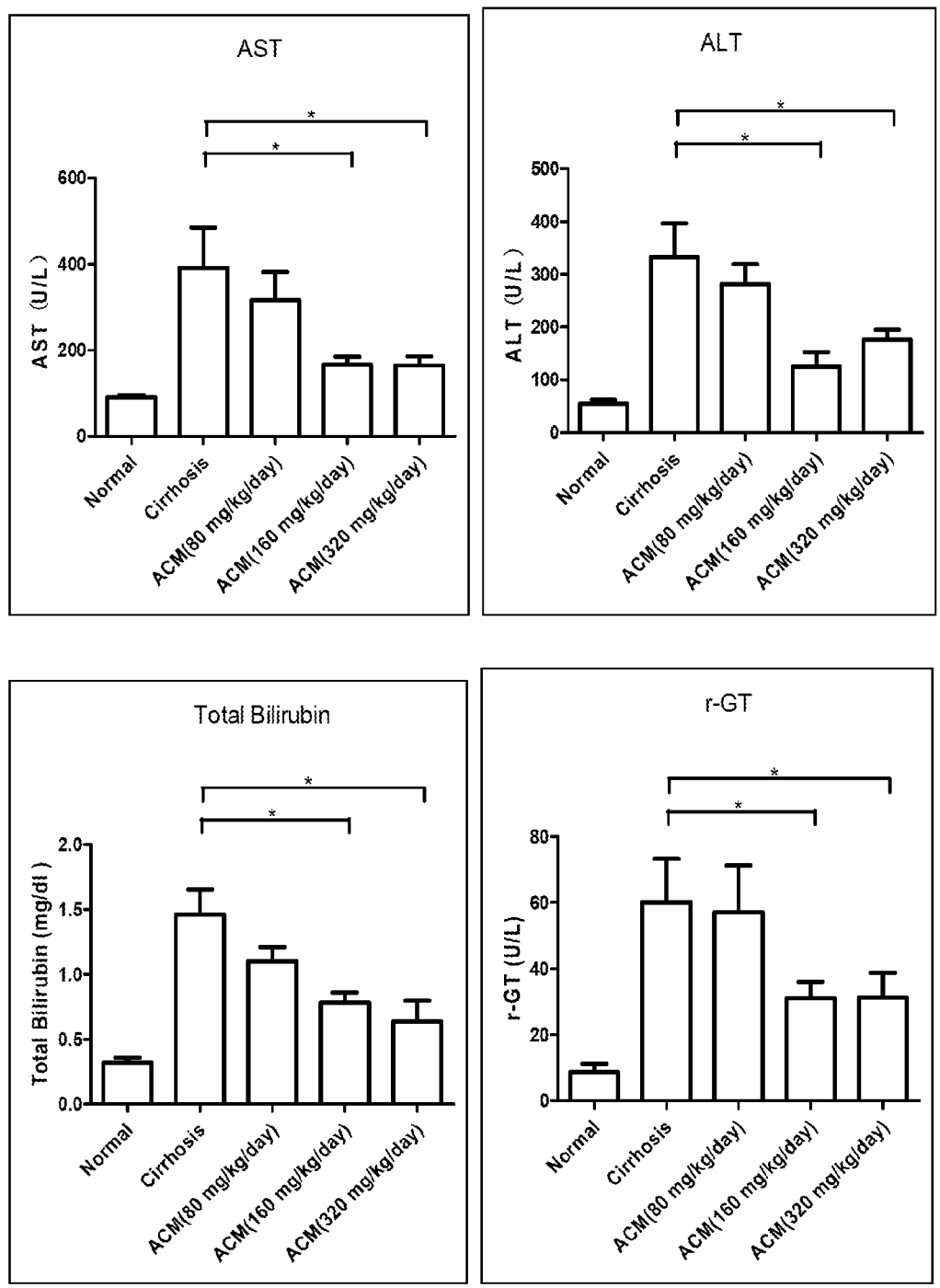
FIG. 1 shows serum parameters about liver damage including Alanine aminotranferease (ALT), aspartate aminotransferase (AST), total bilirubin and Gamma-glutamyl transpeptidase (γ-GT) levels. All parameters shows significantly reduced in the animals fed 160-320 mg/kg/day ACM compared to control group. It means significant hepatocyte protection by ACM>160 mg/kg/day.

The present invention relates to novel uses of compounds from *Antrodia cinnamomea* mycelia and mixtures comprising the compounds. The novel uses comprise whitening skin, combating skin ageing, reducing scar formation, inducing or enhancing liver regeneration, or treating fibrosis or a fibrosis-associated disorder in a subject in need thereof. The compounds have the formula

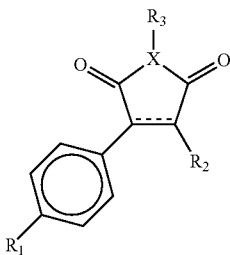

and preferably are selected from
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, and
3R*,4R*-1-hydroxy-3-isobutyl-4-[4-(3-methyl-2-butenyloxy)phenyl]pyrrolidine-2,5-dione.

DETAILED DESCRIPTION OF THE INVENTION

The terms used in the description herein will have their ordinary and common meaning as understood by those skilled in the art, unless specifically defined otherwise. As used throughout the instant application, the following terms shall have the following meanings:

The term "subject" or "individual" refers to an animal. Preferably, the animal is a mammal, e.g. mouse, rat, human, cat, dog, etc. In a preferred embodiment, the subject/individual is a human.

The present invention provides a method for whitening skin comprising: a step of applying a composition to the skin of an individual in need of skin whitening, wherein the composition comprises a compound having the formula

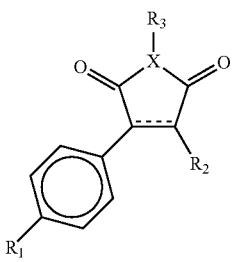

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

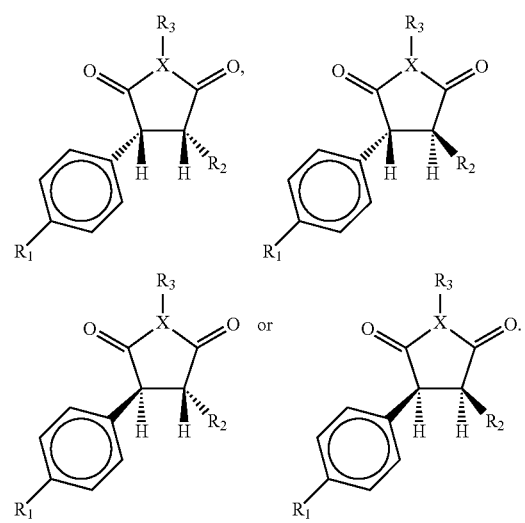

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the composition is a cosmetic or dermatologic preparation for external use. In one preferred embodiment, tyrosinase and thereby biosynthesis of melanin are inhibited by this method.

The present invention also provides a method for whitening skin comprising: a step of applying a mixture to the skin of an individual in need of skin whitening, wherein the mixture comprises water or organic solvent extract of mycelium of *Antrodia cinnamomea*, wherein the extract comprises a compound having the formula

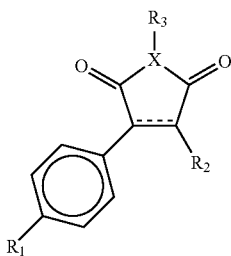

or its tautomeric forms, its stereoisomers, its polymorphs, its salts, or its solvates,
wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl;
$R_3$ is H, hydroxyl, $C_{1-10}$ alkyl, $C_{2-10}$ alkenyl or $C_{2-10}$ alkynyl;
----- denotes a single or double bond;
provided that
if X is O, $R_3$ is absent;
if ----- denotes a single bond, the compound has the formula:

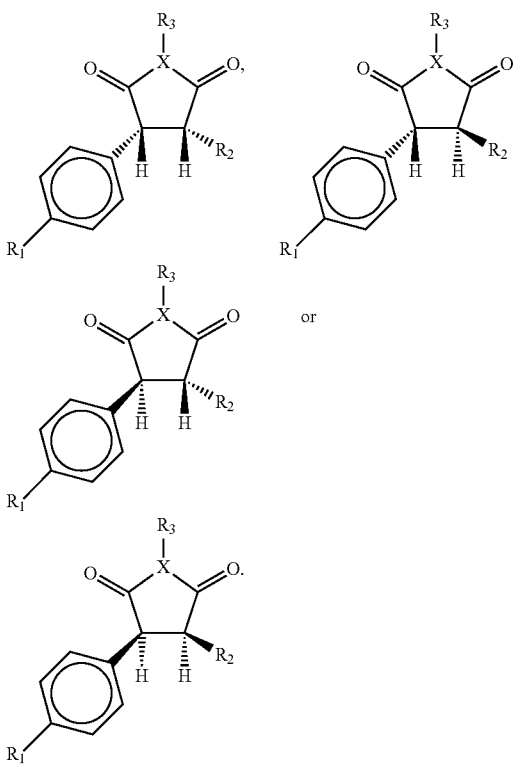

Preferably, the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, or
3R*,4R*-1-hydroxy-3-isobutyl-4-[4-(3-methyl-2-butenyloxy)phenyl]pyrrolidine-2,5-dione.

Preferably, the mixture is a cosmetic or dermatologic preparation for external use. In one preferred embodiment, tyrosinase and thereby biosynthesis of melanin are inhibited by this method.

Preferably, the mycelium of Antrodia cinnamomea is prepared by submerged liquid fermentation. Preferably, the organic solvent includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human.

The present invention further provides a method for combating skin ageing comprising: a step of applying a composition to the skin of an individual in need of combating skin ageing, wherein the composition comprises a compound having the formula

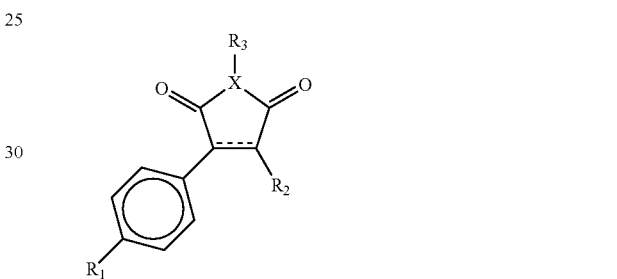

or its tautomeric forms, its stereoisomers, its polymorphs, its salts, or its solvates,
wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl;
$R_3$ is H, hydroxyl, $C_{1-10}$ alkyl, $C_{2-10}$ alkenyl or $C_{2-10}$ alkynyl;
----- denotes a single or double bond;
provided that
if X is O, $R_3$ is absent;
if ----- denotes a single bond, the compound has the formula:

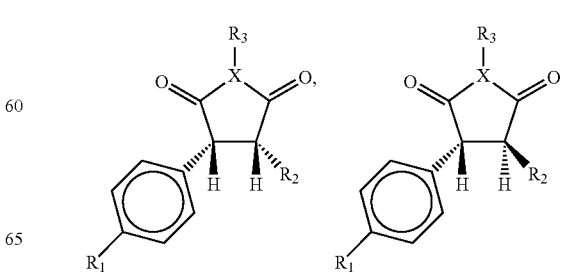

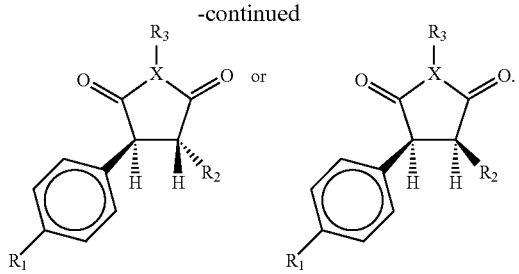

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the skin ageing is caused by oxidative stress, especially the oxidative stress induced by UV exposure. Preferably, the composition is a cosmetic or dermatologic preparation for external use.

The present invention still further provides a method for combating skin ageing comprising: a step of applying a mixture to the skin of an individual in need of combating skin ageing, wherein the mixture comprises water or organic solvent extract of mycelium of *Antrodia cinnamomea*, wherein the extract comprises a compound having the formula

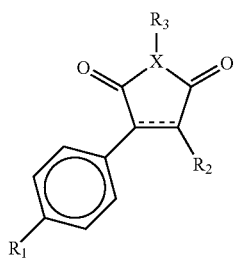

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

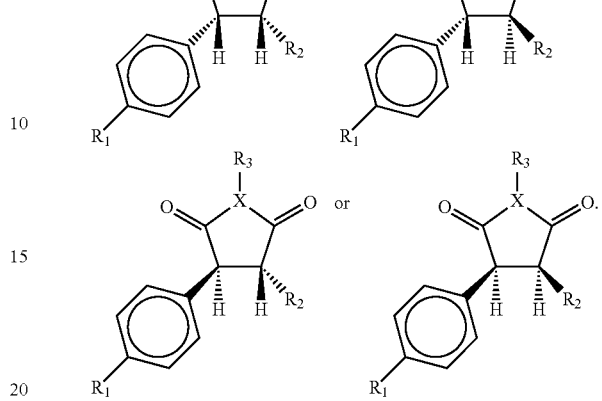

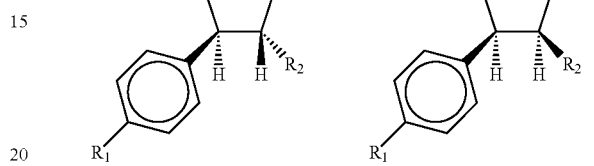

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the skin ageing is caused by oxidative stress, especially the oxidative stress induced by UV exposure. Preferably, the mixture is a cosmetic or dermatologic preparation for external use.

Preferably, the mycelium of *Antrodia cinnamomea* is prepared by submerged liquid fermentation. Preferably, the organic solvent includes but is not limited to alcohol (such as CH3OH, C2H5OH, C3H7OH), ester (such as acetyl acetate), alkane (such as hexane) and halogenated alkane (such as CH3Cl, C2H2Cl2). The preferred organic solvent is ethanol or alcoholic solvent without causing any side effect of human.

The present invention still further provides a method for reducing scar formation, comprising administering to an individual in need thereof an effective amount of a composition comprising a compound having the formula

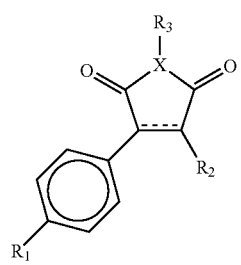

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

===== denotes a single or double bond;

provided that if X is O, $R_3$ is absent;

if ===== denotes a single bond, the compound has the formula:

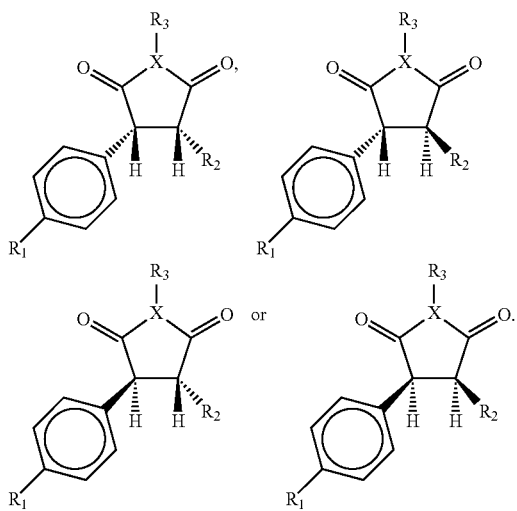

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the individual in need thereof has a wound selected from the group consisting of a laceration; burn; puncture; pressure sore; bed sore; canker sore; trauma, bite; fistula; ulcer; lesion caused by infection; periodontal wound; endodontic wound; burning mouth syndrome; laparotomy wound; surgical wound; incisional wound; contracture after a burn; tissue fibrosis; and a wound resulting from a cosmetic surgical procedure.

Preferably, profibrogenic genes including collagen-1, αSMA, TIMP-1 and TGF-β expression are down-regulated by this method.

The present invention still further provides a method for reducing scar formation, comprising administering to an individual in need thereof an effective amount of a mixture comprising water or organic solvent extract of mycelium of *Antrodia cinnamomea*, wherein the extract comprises a compound having the formula

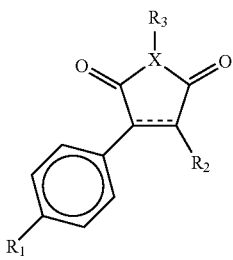

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

===== denotes a single or double bond;

provided that if X is O, $R_3$ is absent;

if ===== denotes a single bond, the compound has the formula:

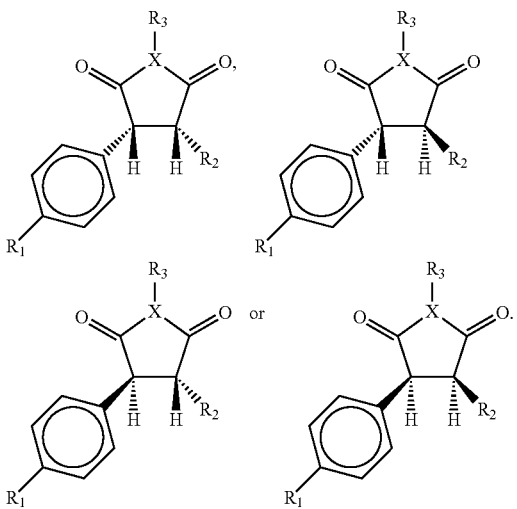

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the individual in need thereof has a wound selected from the group consisting of a laceration; burn; puncture; pressure sore; bed sore; canker sore; trauma, bite; fistula; ulcer; lesion caused by infection; periodontal wound; endodontic wound; burning mouth syndrome; laparotomy wound; surgical wound; incisional wound; contracture after a burn; tissue fibrosis; and a wound resulting from a cosmetic surgical procedure.

Preferably, profibrogenic genes including collagen-1, αSMA, TIMP-1 and TGF-β expression are down-regulated by this method.

Preferably, the mycelium of *Antrodia cinnamomea* is prepared by submerged liquid fermentation. Preferably, the organic solvent includes but is not limited to alcohol (such as CH3OH, C2H5OH, C3H7OH), ester (such as acetyl acetate), alkane (such as hexane) and halogenated alkane (such as CH3Cl, C2H2Cl2). The preferred organic solvent is ethanol or alcoholic solvent without causing any side effect of human.

The present invention still further provides a method for inducing or enhancing liver regeneration, comprising administering to an individual in need thereof an effective amount of a composition comprising a compound having the formula

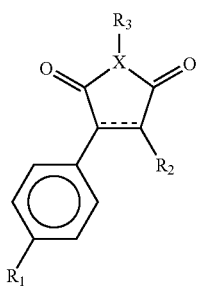

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

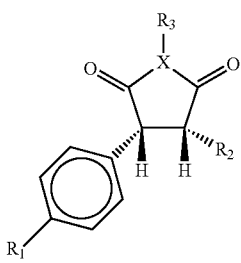 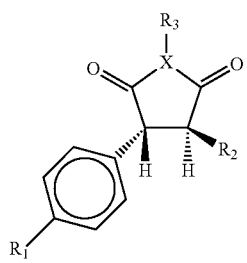

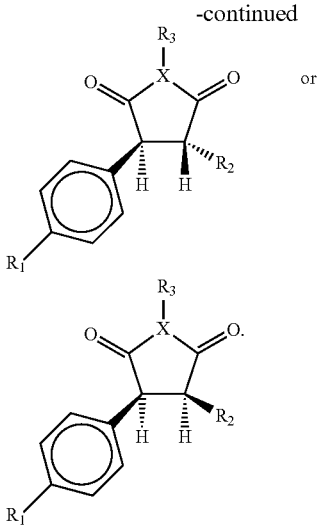

Preferably, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

Preferably, the subject has had a liver resection. In another preferred embodiment, the subject has liver fibrosis or cirrhosis.

The present invention still further provides a method for inducing or enhancing liver regeneration, comprising administering to an individual in need thereof an effective amount of a mixture comprising water or organic solvent extract of mycelium of *Antrodia cinnamomea*, wherein the extract comprises a compound having the formula

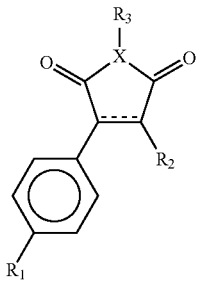

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is H, hydroxyl, $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

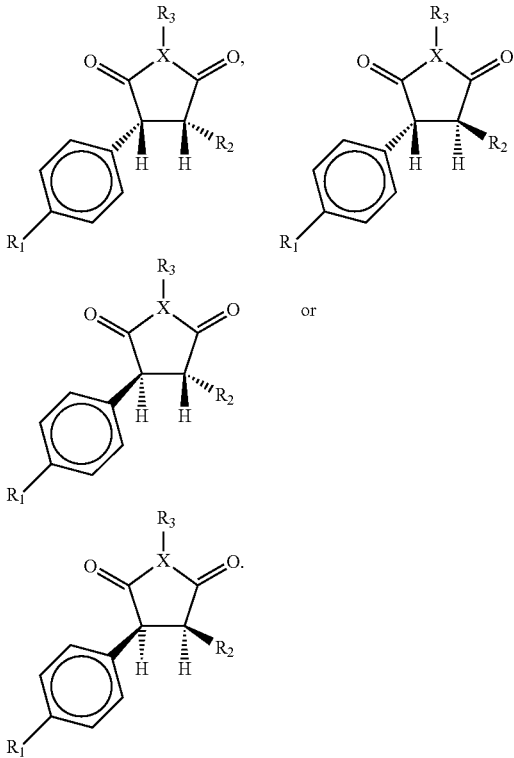

Preferably, the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, or
3R*,4R*-1-hydroxy-3-isobutyl-4-[4-(3-methyl-2-butenyloxy)phenyl]pyrrolidine-2,5-dione.

Preferably, the subject has had a liver resection. In another preferred embodiment, the subject has liver fibrosis or cirrhosis.

Preferably, the mycelium of *Antrodia cinnamomea* is prepared by submerged liquid fermentation. Preferably, the organic solvent includes but is not limited to alcohol (such as CH3OH, C2H5OH, C3H7OH), ester (such as acetyl acetate), alkane (such as hexane) and halogenated alkane (such as CH3Cl, C2H2Cl2). The preferred organic solvent is ethanol or alcoholic solvent without causing any side effect of human.

The present invention still further provides a method of treating fibrosis or a fibrosis-associated disorder, comprising administrating to an individual in need thereof an effective amount of a composition comprising a compound having the formula

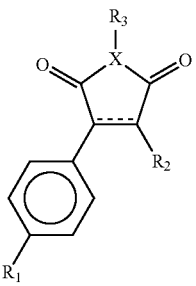

or its tautomeric forms, its stereoisomers, its polymorphs, its salts, or its solvates, wherein X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is hydroxyl, $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

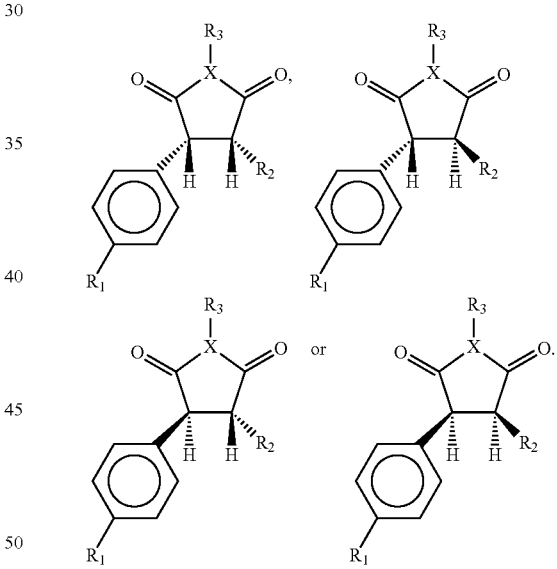

Preferably, the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, or
3R*,4R*-1-hydroxy-3-isobutyl-4-[4-(3-methyl-2-butenyloxy)phenyl]pyrrolidine-2,5-dione.

Preferably, the fibrosis or fibrosis-associated disorder is: liver fibrosis, lung fibrosis, kidney fibrosis, skin fibrosis, cardiac muscle fibrosis, blood vessel fibrosis, scarring, cirrhosis, liver necrosis, chronic obstructive pulmonary disease, diabetic nephropathy, rheumatoid arthritis, fibrosarcomas, scleroderma or a combination thereof.

The present invention still further provides a method of treating fibrosis or a fibrosis-associated disorder, comprising administrating to an individual in need thereof an effective amount of a mixture comprising water or organic solvent extract of mycelium of *Antrodia cinnamomea*, wherein the extract comprises a compound having the formula

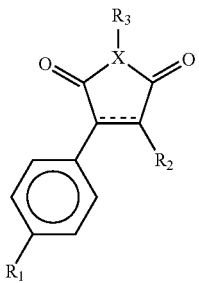

or its tautomeric forms, its stereoisomers, its polymorphs, its salts, or its solvates,
wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl;
$R_3$ is hydroxyl, $C_{1-10}$ alkyl, $C_{2-10}$ alkenyl or $C_{2-10}$ alkynyl;
═══ denotes a single or double bond;
provided that
if X is O, $R_3$ is absent;
if ═══ denotes a single bond, the compound has the formula:

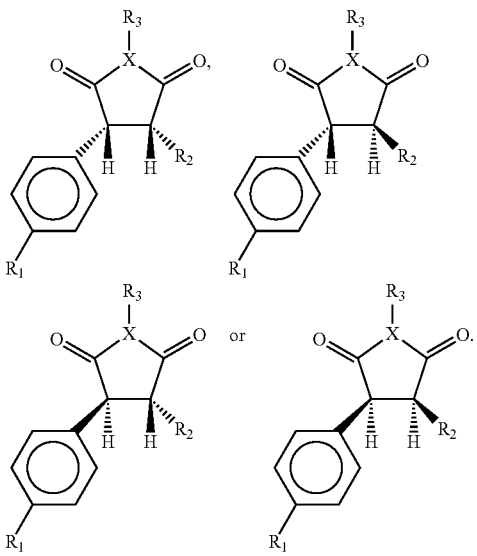

Preferably, the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, or
3R*,4R*-1-hydroxy-3-isobutyl-4-[4-(3-methyl-2-butenyloxy)phenyl]pyrrolidine-2,5-dione.

Preferably, the fibrosis or fibrosis-associated disorder is: liver fibrosis, lung fibrosis, kidney fibrosis, skin fibrosis, cardiac muscle fibrosis, blood vessel fibrosis, scarring, cirrhosis, liver necrosis, chronic obstructive pulmonary disease, diabetic nephropathy, rheumatoid arthritis, fibrosarcomas, scleroderma or a combination thereof.

Preferably, the mycelium of *Antrodia cinnamomea* is prepared by submerged liquid fermentation. Preferably, the organic solvent includes but is not limited to alcohol (such as CH3OH, C2H5OH, C3H7OH), ester (such as acetyl acetate), alkane (such as hexane) and halogenated alkane (such as CH3Cl, C2H2Cl2). The preferred organic solvent is ethanol or alcoholic solvent without causing any side effect of human.

The present invention further provides a skin whitening formulation comprising water or organic solvent extract of fermented mycelium of *Antrodia cinnamomea* as an active ingredient to provide whitening, wherein the extract comprises at least one compound selected from the group consisting of
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, and
3R*,4R*-1-hydroxy-3-isobutyl-4-[4-(3-methyl-2-butenyloxy)phenyl]pyrrolidine-2,5-dione,
wherein the concentration of
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
or a mixture of
3R*,4S*-1-hydroxy-3-isobutyl-4-[4-(3-methyl-2-butenyloxy)phenyl]pyrrolidine-2,5-dione and
3R*,4R*-1-hydroxy-3-isobutyl-4-[4-(3-methyl-2-butenyloxy)phenyl]pyrrolidine-2,5-dione is equal or larger than 3 μM.

Preferably, the fermented mycelium of *Antrodia cinnamomea* is prepared by submerged liquid fermentation.

Preferably, the formulation is a cosmetic or dermatologic preparation for external use, and inhibits tyrosinase and biosynthesis of melanin.

The present invention also further provides a skin ageing combating formulation comprising water or organic solvent extract of fermented mycelium of *Antrodia cinnamomea* as an active ingredient to provide skin ageing combating, wherein the extract comprises at least one compound selected from the group consisting of
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione, and
3R*,4R*-1-hydroxy-3-isobutyl-4-[4-(3-methyl-2-butenyloxy)phenyl]pyrrolidine-2,5-dione,
wherein the concentration of
3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
or a mixture of
3R*,4S*-1-hydroxy-3-isobutyl-4-[4-(3-methyl-2-butenyloxy)phenyl]pyrrolidine-2,5-dione and
3R*,4R*-1-hydroxy-3-isobutyl-4-[4-(3-methyl-2-butenyloxy)phenyl]pyrrolidine-2,5-dione is equal or larger than 3 µM.

Preferably, the fermented mycelium of *Antrodia cinnamomea* is prepared by submerged liquid fermentation.

Preferably, the formulation is a cosmetic or dermatologic preparation for external use.

In an embodiment, the skin ageing is caused by oxidative stress. In an embodiment, the oxidative stress is induced by UV exposure.

The compositions or the mixtures of the present invention can be used in the form of a solid, a solution, an emulsion, a dispersion, a micelle, a liposome, and the like, wherein the compositions or the mixtures contain one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The compositions or the mixtures of the invention may be in a form suitable for oral use, for example, as tablets, troches, lozenges, aqueous or oily suspensions, dispersible powders or granules, emulsions, hard or soft capsules, or syrups or elixirs. Compositions or mixtures intended for oral use may be prepared according to any method known to the art for the manufacture of pharmaceutical products and such compositions or mixtures may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452 and 4,265,874, to form osmotic therapeutic tablets for controlled release.

In some cases, compositions for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The compositions or the mixtures may also be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compositions or mixtures contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

In known manner, the compositions of the invention can also comprise the adjuvants usual in the cosmetics and dermatological fields, such as hydrophilic or lipophilic gelling agents, humectants, such as glycerol and sorbitol, fatty-phase thickeners, preservatives, antioxidants, electrolytes, solvents, fragrances, fillers, screening agents, pigments, odor absorbers, coloring materials and metal-chelating agents. The amounts of these various adjuvants are those conventionally employed in the fields under consideration, for example from 0.01 to 20% of the total weight of the composition. These adjuvants, depending on their nature, can be introduced into the lipophilic phase or into the hydrophilic phase. These adjuvants, and their concentrations, must be such that they do not adversely affect the cosmetic and/or dermatological properties of the compositions according to the invention.

Exemplary are hydrophilic gelling agents, of carboxyvinyl polymers (carbomer), acrylic copolymers, such as acrylate/alkylacrylate copolymers or acrylate copolymers, polyacrylamides, polysaccharides, natural gums and clays, and mention may be made, as lipophilic gelling agents, of modified clays, such as bentones, metal salts of fatty acids, hydrophobic silica or silicone gums.

EXAMPLES

The examples below are non-limiting and are merely representative of various aspects and features of the present invention.

Example 1

ACM for Liver Fibrosis—to Treat Cirrhotic Animals by ACM with 3 Different Dosages for 6 Weeks Method
Cirrhotic Animal Model:
Male Wistar rats (150-180 g) at 7 weeks of age were obtained from the Animal Center of National Taiwan University. The rats were housed in standard conditions, and all the experiments were conducted in accordance with the "Guide for the Care and Use of Laboratory Animals" prepared by the Institutional Animal Care and Use Committee of National Taiwan University. The rats were given DEN solution daily (Sigma, St Louis, Mo.) as the sole source of drinking water for 9 weeks, followed by 2 weeks of regular water. It starts with 100 ppm (vol/vol) in the first week. The average BW of the animals was measured once a week, and the concentration of DEN in their drinking water was adjusted in proportion to the BW each week relative to that of the first week.

Preparation of Extraction:

Powdered mycelia of *Antrodia cinnamomea* (ACM), from Simpson Biotech Co. Ltd., Taiwan, were extracted with $CHCl_3$ 3 h under reflux. Finely ground ACM with three different dosages (80, 160 and 320 mg/kg) were prepared with sterile distilled water and fed to rats through a gastric tube everyday from $5^{th}$ to $11^{th}$ week. Some of the animals were sacrificed in $11^{th}$ week and their livers were sampled for pathologic examination and gene expression assay.

Liver Regeneration Calculation:

Two weeks after the withdrawal of the DEN solution (in $11^{th}$ week), some of the animals were anesthetized with 90 mg/kg ketamine and 5 mg/kg xylazine. After a midline laparotomy, 70% PHx was performed by resecting the median and left lateral lobes. The MRI scans were performed before and after operation immediately, and scanned again on days $7^{th}$ after operation. The liver borders were electronically drawn in each 1-mm thick MR slice and the hepatic "cut surface area" was measured automatically (standard software, Advantage Workstation; GE Healthcare, Waukesha, Wis.). According to Cavalieri's method, addition of all measured liver section surfaces results in total liver volume (area [$mm^2$]×slice thickness [mm]). After the last MRI scan, these animal were sacrificed and their livers were sampled for BrdU staining.

Percent liver regeneration was calculated for each individual animal as:

$$\% \text{ Liver regeneration} = ((L7-L0) \times 100)/(L-1-L0)$$

Where L7 is liver volume at day $7^{th}$, L0 is liver volume immediately after partial hepatectomy and L-1 is liver volume prior to partial hepatectomy.

Biochemical Analysis of Serum

Samples of 1 ml blood were gathered from the retro-orbital plexus of each mouse and immediately centrifuged at 1300×g at 4° C., plasma was kept at −20° C. for liver function tests. Alanine aminotranferease (ALT), aspartate aminotransferase (AST), total bilirubin and Gamma-glutamyl transpeptidase (γ-GT) levels were determined using commercial enzymatic kits with a colorimetric analyzer (Dri-Chem 3000, Fuji Photo Film Co, Tokyo, Japan).

Measurement of Hydroxyproline Content in the Liver.

Liver collagen content was determined from the tumor-free liver samples by quantifying the levels of hydroxyproline. In brief, liver sample (between 15 and 25 mg) in an Eppendorf tube containing 20 mL of 6 N HCl was carefully ground using a pestle. Additional 6 N HCl was then added to make a total volume of 30 mL/mg tissue and in a way to wash down the residual tissue fragments on the pestle. The ground tissue in HCl was hydrolyzed at 120∞C for 16 h. After brief cooling on ice and centrifugation at 8000 g for 10 min, the supernatant was removed to a new tube; the lost volume by evaporation was replenished by water. Equal volume of 6 N NaOH was added and mixed, and the solution was adjusted to pH 4-9 using litmus paper. Forty microliters of the neutralized sample solution was removed to a 96-well ELISA plate and oxidized in each well with a solution containing 5 mL of 7% Chloramine T (Sigma, St Louis, Mo., USA) and 20 mL of acetate/citrate buffer (57 g sodium acetate.3H2O, 37.5 g trisodium citrate.2H2O, 5.5 g citric acid.H2O, 385 mL isopropanol, and dissolved in $H_2O$ to a final volume of 1 L). Thereafter 150 mL of Ehrlich's solution was added. The Ehrlich's solution was prepared by dissolving 2 g of pdimethylamino-benzaldehyde (Sigma) in 3 mL of 60% HClO4 (Merck, Darmstadt, Germany) and then mixed with 9 mL of isoprapanol. The final mixture was incubated at 60° C. for 35 min and then at room temperature for 10 min, and the absorbance was determined at 560 nm. Standard solutions containing 100, 80, 60, 40, 20 and 0 mg/mL of authentic 4-hydroxy-L-proline (Sigma) were treated likewise. The standard curve was linear in this range (r=0.98). The value of the liver hydroxyproline level was expressed as mg/g wet tissue.

Immunohistochemistry and Histological Staining.

Liver samples were fixed in formalin and embedded in paraffin for Sirius red staining. For detecting hepatic fibrosis, liver sections were stained for 1 hour with 0.1% (wt/vol) Sirius red (Sigma, St Louis, Mo.) in a saturated aqueous solution of picric acid (Wako, Osaka, Japan). After staining, the slides were rinsed with two changes of acidified water [0.5% (wt/wt) glacial acetic acid in H2O], and then dehydrated in three changes of 100% ethanol. The slides were cleared in xylene, mounted in a resinous medium, and then observed under a light microscope. Sirius red-positive areas were measured using the Digital Camera System HC-2500 and Image-Pro Plus. For detecting the regeneration capacity of liver after partial resection, immunostaining of BrdU was performed for liver 7 days after 70% hepatectomy as described previously. For staining of BrdU, sections were incubated with a monoclonal mouse anti-BrdU 1:100 (MO744 clone BU20A; DAKO Sweden AB) for 60 min, followed by incubation of the secondary antibody, a biotinylated polyclonal rabbit anti-mouse 1:400 (E0464; DAKO Sweden AB), for 25 min. Sections were then incubated with ABC vectastain standard kit (PK 6100; Vector Laboratories, Burlingame, Calif.) for 30 min and developed with DAB Immpact (Vector Laboratories) substrate for 5 min. Sections were counterstained with hematoxylin (Mayers Hematoxylin; Histolab, Göteborg, Sweden). The labeling index of BrdU was calculated as the ratio between the positively stained hepatocyte nuclei, respectively, to the total numbers of hepatocytes. The cumulative mean value from 15 randomly counted fields of the sections was calculated under light microscopy (400×).

Quantitative Real-Time Reverse Transcription Polymerase Chain Reaction (RT-PCR) Analysis of Collagen Expression and Oxidative Stress Sample tissues of rat livers were measured about 0.5×0.5 cm in area. Each of tissue was homogenized in 1 mL of TRIzol buffer (Invitrogen, Carlsbad, Calif., USA) with a motorized pestle, and then mixed with 0.5 mL chloroform/isoamyl alcohol (24:1), and was centrifuged at 12,000×g for 10 min at 4° C. The supernatant was transferred to a fresh tube, and isopropanol was added, mix well and stored at −80° C. overnight. The reaction mixture was centrifuged at 12,000×g for 30 min at 4° C. to produce a rude RNA pallet, the pellet was washed with 70% ethanol and air-dried. The concentrations of total RNA were measured by absorbance at 260 nm using a NanoDrop ND-1000 (NanoDrop, USA). Reverse transcription reaction was performed using a commercially available set of High Capacity RNA-to-cDNA Kit (Applied Biosystems, USA). cDNA was prepared from 2 μg of total RNA per 20 μl reaction, according to the manufacturer's instructions—37° C. for 60 minutes, 95° C. for 5 minutes, and hold at 4° C. The resulting cDNA was to a final concentration of 100 ng/μl and constituted a matrix in further experiments. Amplification and detection the gene expression by real-time PCR were performed using StepOne plus Real-time PCR System (Applied Biosystems, USA). Samples were assayed in a 10 μl reaction mixture containing 2 μl of template DNA, 5 μl of 2× TaqMan PCR Master Mix (Applied Biosystems, Life Technologies, Foster City, Calif., USA), 0.5 μl of 20× assay mix containing probe, forward and reverse primer (Applied Biosystems, Life Technologies, Foster City, Calif., USA), whereby qPCR targets with the following information were used: (a) Rat α-SMA, Assay ID Rn01759928_g1, (b) Rat TIMP, Assay ID Rn00587558_m1, (c) Rat TGF-β1, Assay ID Rn00572010_m1, (d) Rat Collagen I, Assay ID Rn 01463838_m1, (e) Rat CuZnSOD, Assay ID Rn00566938_m1, (f) Rat MnSOD, Assay ID Rn00690587_g1, (g) Rat Catalase, Assay ID Rn00560930_m1, (h) Rat Glutathione peroxidase, Assay ID Rn00577994_g1, (i) Rat NADPH oxidase, Assay ID Rn00585380_m1 and (j) Rat GAPDH, Assay ID Rn1462662_g1. To control variation in mRNA concentration, all results were normalized to the housekeeping gene, GAPDH. Relative quantitation was performed using the comparative ΔΔCt method according to the manufacture's instructions. The cycling conditions used were as follows: 50° C. for 2 min, 95° C. for 10 min followed by 40 cycles of 95° C. for 15 s and 60° C. for 1 min each.

Result

Improvement of Hepatic Damage Parameters.

At the end of the experiment, the serum parameters about liver damage including Alanine aminotranferease (ALT), aspartate aminotransferase (AST), total bilirubin and Gamma-glutamyl transpeptidase (γ-GT) levels all showed significantly reduced in the animals fed 160-320 mg/kg/day ACM compared to control group (FIG. 1). It means significant hepatocyte protection by ACM>160 mg/kg/day.

Figure 2:
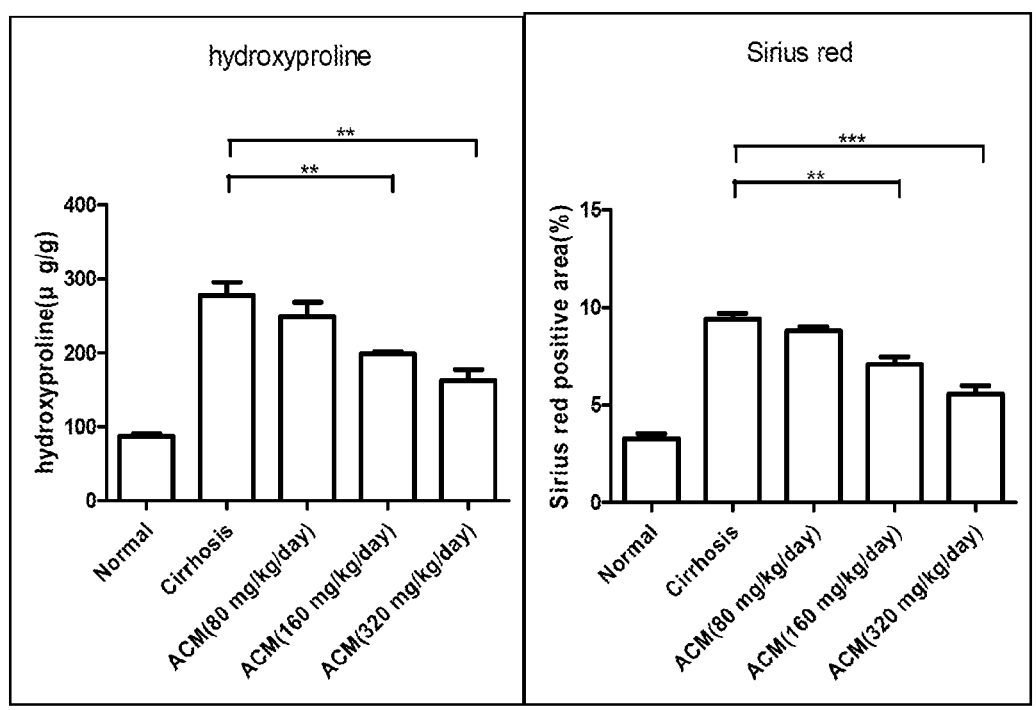
FIG. 2 shows comparison of the differences in hydroxyproline levels between the livers in treatment groups and control group and in microscopically Sirius red-positive areas also. The results show markedly ameliorated liver cirrhosis in animals fed 160-320 mg/kg/day ACM.

Amelioration of Liver Fibrosis:

To assess the antifibrotic effects of ACM, a comparison of the differences in hydroxyproline levels between the livers in treatment groups and control group and in microscopically Sirius red-positive areas also. The results showed markedly ameliorated liver cirrhosis in animals fed 160-320 mg/kg/day ACM (FIG. 2).

Reduce of Pre-Fibrotic Gene Expression

Figure 3:
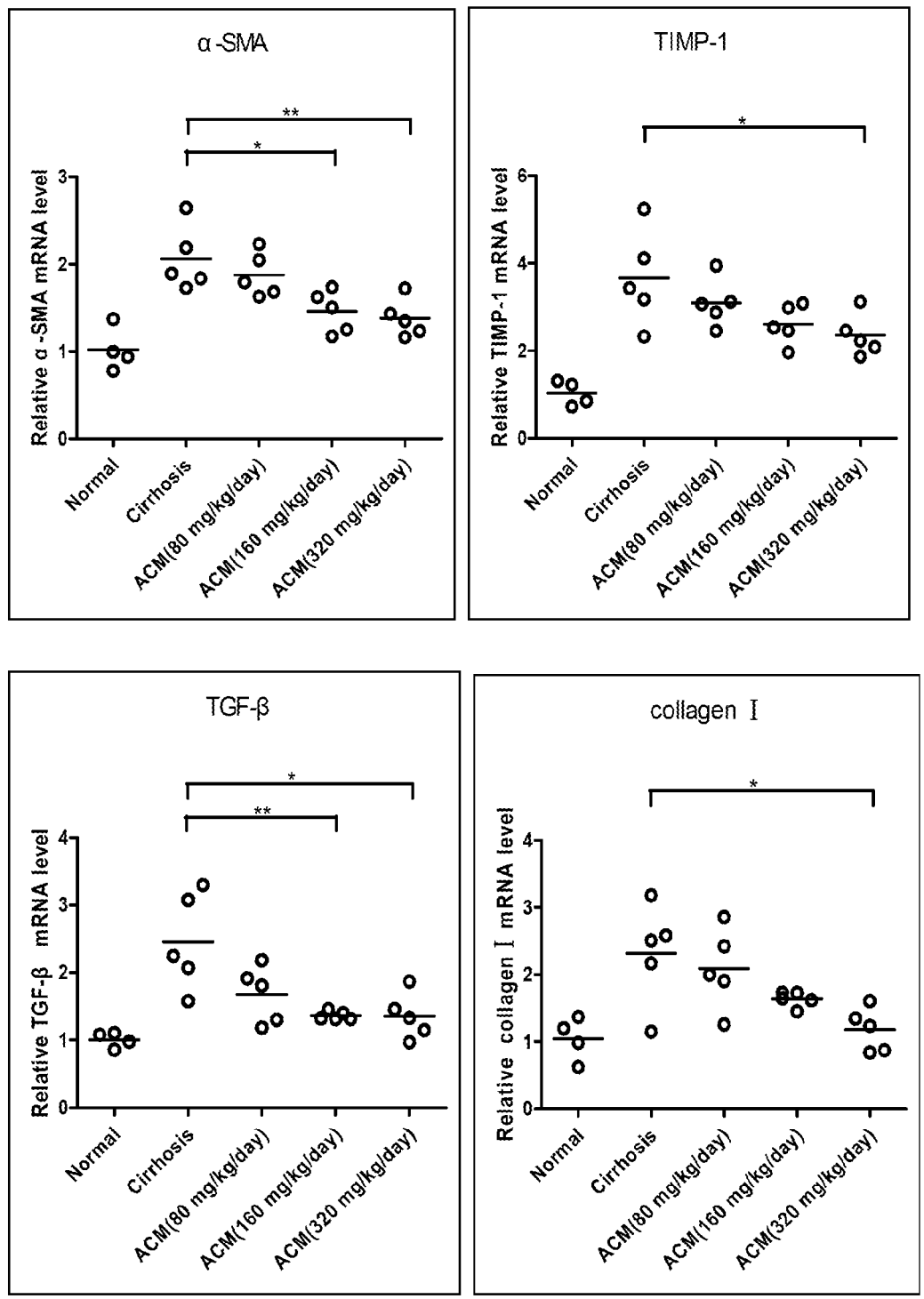
FIG. 3 shows reduce of pre-fibrotic gene expression after treatment of ACM.

After treatment of ACM, the expression of pre-fibrotic genes including α-SMA, TIMP, and TGF-β1 were reduced significantly in the animals fed 160-320 mg/kg/day ACM, and significantly down-regulated Collagen type I gene expression was noted in 320 mg/kg/day group (FIG. 3).

Figure 4A:
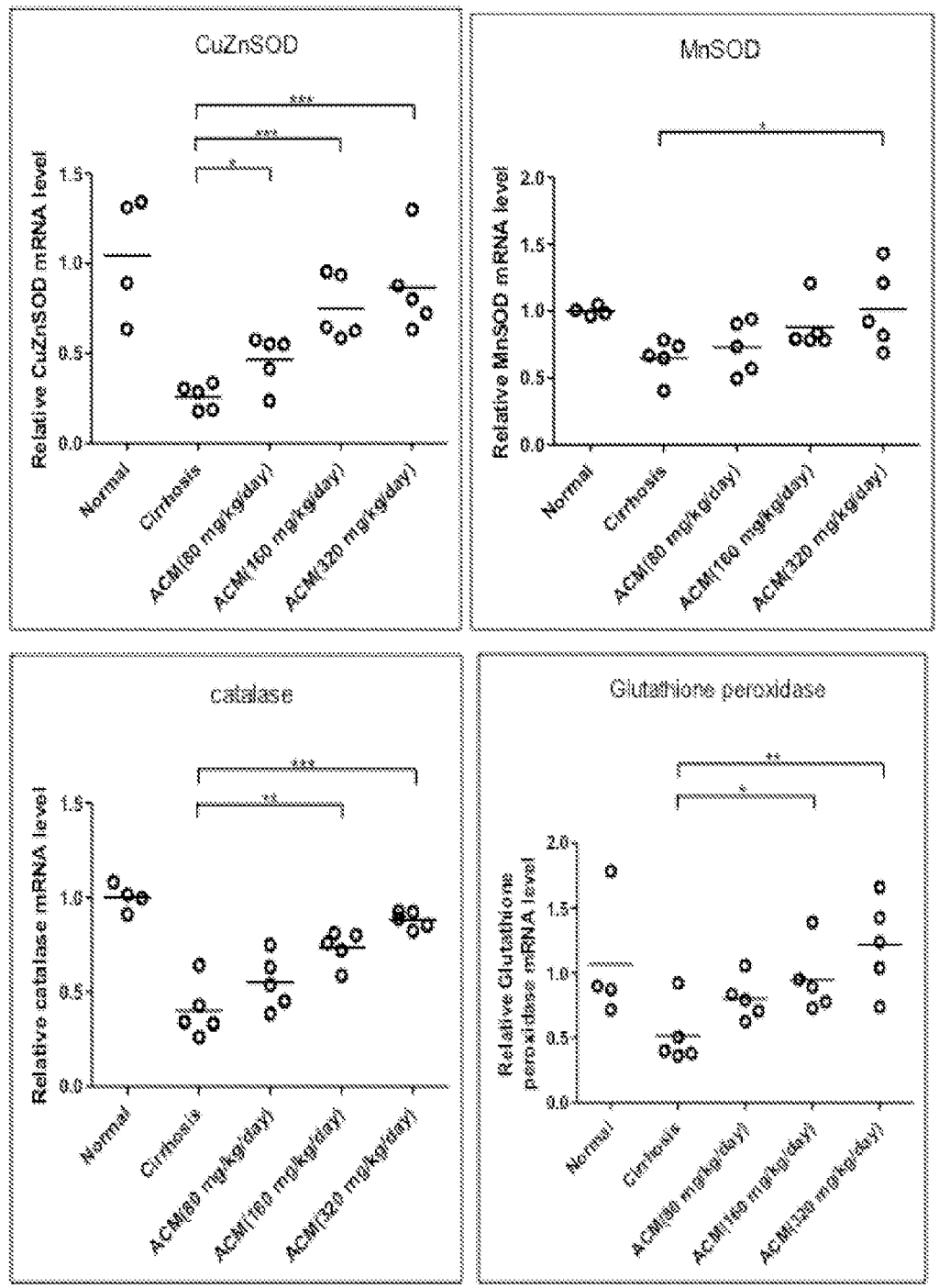
FIGS. 4A and 4B show decrease of oxidative stress after treatment of ACM.
Figure 4B:
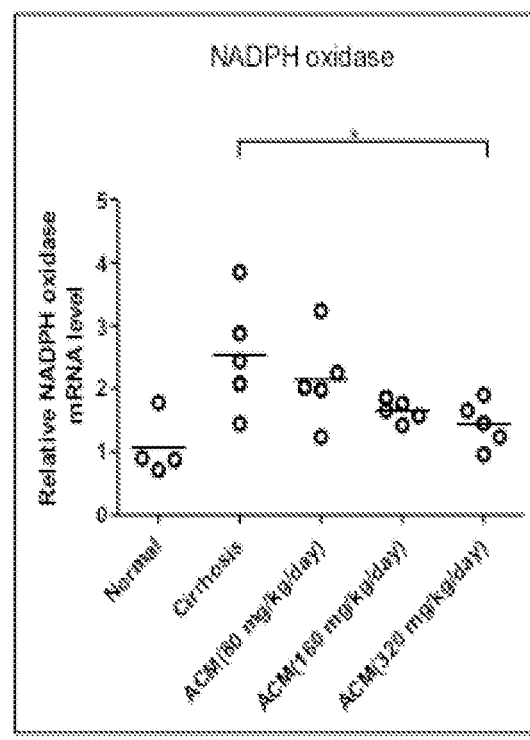

Decrease of Oxidative Stress:

After treatment of ACM, the gene expression of anti-oxidant enzyme including CuZnSOD, MnSOD, Catalase and Glutathione peroxidase were up-regulated prominently, especially in the animals fed with 320 mg/kg/day, all these gene expressed were increased significantly, and the gene expression of NADPH oxidase, a main enzyme to generate reactive oxidative species (ROS), was down-regulated. It means the treatment of 320 mg/kg/day ACM can decrease oxidative stress accompanied with liver fibrosis significantly (FIGS. 4A and 4B).

Figure 5:
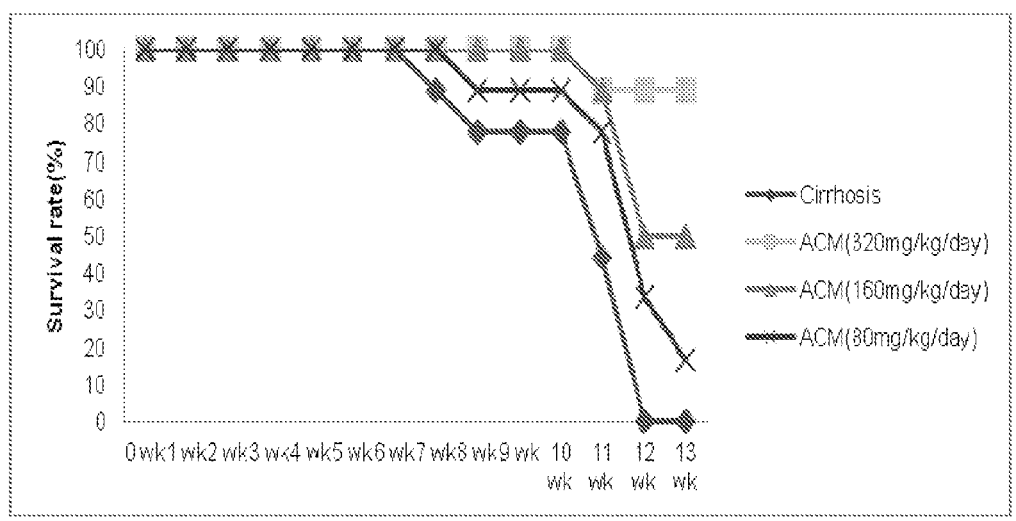
FIG. 5 shows the life span of cirrhotic animal.

Prolong the Life Span of Cirrhotic Animal:

During the induction of liver cirrhosis, some of the animals were monitored for life span. All the control animal were dead after $12^{th}$ week, however, the survival rates in animals fed with 80, 160, 320 mg/kg/day ACM were 33%, 50% and 90% respectively (FIG. 5). The prolongation of liver span in cirrhotic animals was noted after treatment of ACM, and 160-320 mg/kg/day ACM could prolong the survival of cirrhotic animals significantly.

Figure 6:
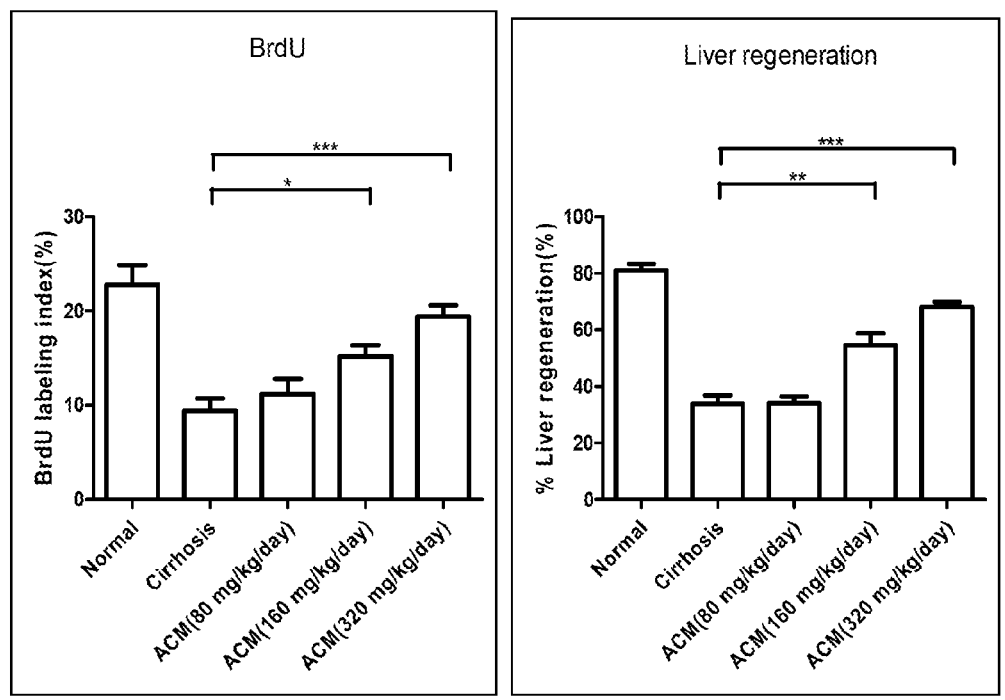
FIG. 6 shows restoration of liver regeneration capacity after treatment of ACM.

Restoration of Liver Regeneration Capacity after Hepatectomy:

After 70% hepatectomy, the survival rate in control group, 80, 160 and 320 mg/kg/day ACM group on $7^{th}$ day after operation were 12.5%, 25%, 75% and 87.5% respectively. The food intake is only 55% of the amount before operation in control group. However, the animals in treatment groups showed no any appetite loss on $7^{th}$ day after operation. The liver regeneration was presented as liver size and BrdU-positive area, and both BrdU labeling index and liver regeneration percentage showed significant increase in the animal received 160-320 mg/kg/day ACM treatment (FIG. 6).

Example 2

Hepasims for Liver Fibrosis—Cellular Study for Hepasims

The experiment was designed to verify the hypothesis that the anti-fibrotic effect of ACM was derived from hepasims.

Method

Cells

The AML12 (mouse hepatocyte) cells were obtained from the BCRC (Bioresource Collection and Research Center) and cultured in Dulbecco's modified Eagle media (DMEM, Gibco by Invitrogen) with 1% antibiotic antimycotic (Gibco by Invitrogen) and 15% fetal bovine serum (Gibco by Invitrogen). The human Hepatic Stellate Cell, HSC cell line was obtained from the ScienCell Research Laboratory (USA) and cultured in complete medium, Stellate Cell Medium (ScienCell Research Laboratory) with 2% fetal bovine serum (ScienCell Research Laboratory), 1% stellate cell growth supplement (ScienCell Research Laboratory) and 1% penicillin/streptomycin solution (ScienCell Research Laboratory). It is well known that TGF-β1 can activation of HSC, which was used as a positive control, the HSC cells were seeded in plate for 24 h and then the cells were replaced with medium containing 10 ng TGF-β1 (PeproTech, USA). For primary hepatic stellate cell isolation, C57BL/6 mice were anesthetized by intraperitoneal injection of ketamine and xylazine. The suprahepatic inferior vena cava was ligated and the infrahepatic inferior vena cava was cannulated. Mouse livers were perfused in situ with 0.5 mM EGTA containing calcium-free salt solution (8 ml/min, 37° C. for 5 minutes), followed by perfusion with 2-step 0.05% collagenase D and pronase containing buffer (Roche Molecular Biochemicals, Indianapolis, Ind.) for 5 and 10 minutes, respectively. The harvested liver was minced gently on a Petri dish and additional incubation with protease containing buffer at 37° C. for 25 minutes. Then, the liver was filtered with 70 μm cell strainer. Cells were centrifuged and collected followed by 8.2% Nycodenz (Accurate Chemical and Scientific Corp.). The cell lines were cultured at 37° C. in a humidified atmosphere containing 5% $CO2$.

Preparation of Hepasim Compounds:

Hepasim compounds, i.e. compounds A-E used in the following experiments, were equal to compounds 1-5 disclosed in U.S. Pat. No. 7,109,232, and were also called Antrodin A-E.

Compound A 3-isobutyl-4-[4-(3-methyl-2-butenyloxy)phenyl]furan-2,5-dione

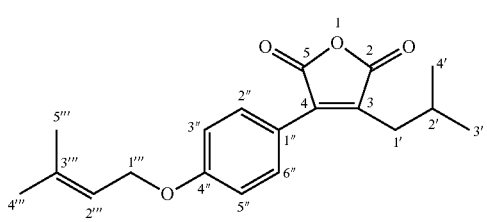

(A)

Compound B 3-isobutyl-4-[4-(3-methyl-2-butenyloxy)phenyl]-1H-pyrrol-2,5-dione

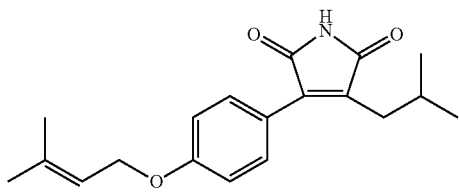

(B)

Compound C 3-isobutyl-4-[4-(3-methyl-2-butenyloxy)phenyl]-1H-pyrrol-1-ol-2,5-dione

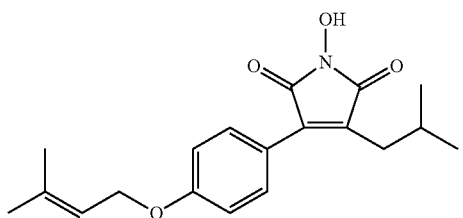

(C)

Compound D (3R*,4S*)-1-hydroxy-3-isobutyl-4-[4-(3-methyl-2-butenyloxy)phenyl]pyrrolidine-2,5-dione

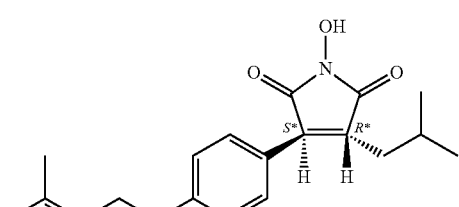

(D)

Compound E (3R*,4S*)-1-hydroxy-3-isobutyl-4-[4-(3-methyl-2-butenyloxy)phenyl]pyrrolidine-2,5-dione

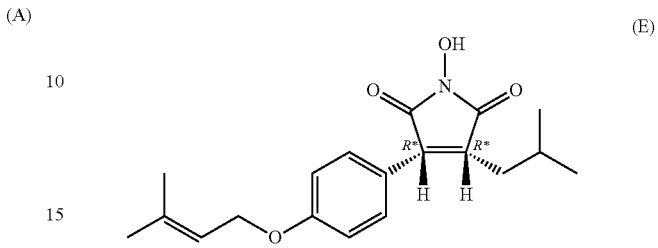

(E)

The methods for preparing these five compounds were the same as those disclosed in U.S. Pat. No. 7,109,232.

It was noted that in the following experiments, "compound D" referred to a racemic mixture of compound D and compound E, and in which the ratio of compound D to compound E was preferably 1:1~2:1. In an embodiment, the ratio of compound D to compound E is about 1.62:1.

Effects of Hepasim Compounds on Hepatocyte Damage Induced by $H_2O_2$ Treatment in AML12 Liver Cell Line:

To determine hepatoprotective effects of these compounds on hepatocytes in response to $H_2O_2$ (a known inducer of cell damage), the effects on hepatocyte damage were examined by measuring Alanine aminotranferease (ALT) levels in the supernatant secreted from AML12 cell line. Cells were cultured in 1% FBS containing Hepasim Compounds (A, B, C, and D) by different concentrations (3 and 10 μM) for 72 hrs and then treated with $H_2O_2$ for 2 hrs. ALT levels in the supernatant were measured using an Infinity ALT assay kit (Thermo Scientific).

Cellular Reactive Oxygen Species Assay after Hepasim Compounds Treatment

A commercially available kit (# K264-100, BioVision) was used to measure glutathione (GSH), and oxidized glutathione (GSSG). The GSH/GSSG ratio was determined from these data. The assay was conducted with several modifications to the manufacturer's directions. Briefly, cellular pellet (~10 mg) was homogenized immediately, and take 60 μl of each sample to a prechilled tube containing Perchloric Acid and centrifuged at 13,000×g for 2 min, collect supernatant and stored at −80° C. until analyzed. The assay was conducted as described by the manufacturer. Briefly, cold 3N KOH was added to each sample mixed, and centrifuged at 13,000×g for 10 min. Ten microliters of each sample and the appropriate buffer and 90 μl of Assay Buffer to detect GSH and 10 μl of glutathione reductase were mixed to detect total glutathione and 10 μl of GSH Quencher to detect GSSG and incubated at room temperature for 40 min and the absorbance of each sample was read at 340/420 nm for 3 min. The protein concentration for each sample was determined via a DC protein concentration assay (Bio-Rad). Signals from each sample were normalized to the corresponding protein content of that sample.

RNA Extraction of Cell and Quantitative Reverse Transcription-Polymerase Chain Reaction (RT-PCR)

Exponentially growing cells were harvested and seeded in a 6-well microtiter plate. Each well of cells were collected to eppendrof in 1 mL of TRIzol buffer (Invitrogen, Carlsbad, Calif., USA), and then mixed with 0.5 mL chloroform/isoamyl alcohol (24:1), eppendrofs were centrifuged at 12,000×g for 10 min at 4° C. The supernatant was transferred to a fresh tube, and isopropanol was added, mix well and stored at −80° C. overnight. The reaction mixture was centrifuged at 12,000×g for 30 min at 4° C. to produce a rude RNA pallet, the pellet was washed with 70% ethanol and air-dried. The concentrations of total RNA were measured by absorbance at 260 nm using a NanoDrop ND-1000 (NanoDrop, USA).

Reverse transcription reaction was performed using a commercially available set of High Capacity RNA-to-cDNA Kit (Applied Biosystems, USA). cDNA was prepared from 2 µg of total RNA per 20 µl reaction, according to the manufacturer's instructions—37° C. for 60 minutes, 95° C. for 5 minutes, and hold at 4° C. The resulting cDNA was to a final concentration of 100 ng/µl and constituted a matrix in further experiments.

Amplification and detection the gene expression by real-time PCR were performed using StepOne plus Real-time PCR System (Applied Biosystems, USA). Samples were assayed in a 10 µl reaction mixture containing 2 µl of template DNA, 5 µl of 2× TaqMan PCR Master Mix (Applied Biosystems, Life Technologies, Foster City, Calif., USA), 0.5 µl of 20× assay mix containing probe, forward and reverse primer (Applied Biosystems, Life Technologies, Foster City, Calif., USA), whereby qPCR targets with the following information were used: (a) α-SMA, Assay ID Rn01759928_g1, (b) TIMP-1, Assay ID Rn00587558_m1, (c) TGF-β1, Assay ID Rn00572010_m1, (d) Collagen I, Assay ID Rn 01463838_m1, (e) GAPDH, Assay ID Rn1462662_g1. To control variation in mRNA concentration, all results were normalized to the housekeeping gene, GAPDH. Relative quantitation was performed using the comparative ΔΔCt method according to the manufacturer's instructions. The cycling conditions used were as follows: 50° C. for 2 min, 95° C. for 10 min followed by 40 cycles of 95° C. for 15 s and 60° C. for 1 min each.

Preventive Effects of Hepasim Compounds on Profibrogenic Gene Expression in Primary Hepatic Satellite Cell:

Mouse primary HSC were cultured in DMEM containing 10% FBS for 7 days for full-activation without any profibrogenic agents. The cells will be activated to fibrogenesis spontaneously under nature condition before 7$^{th}$ day. Cells were exposed to Hepasim compounds by two different concentrations for 72 hrs. Then, RNA was extracted and subsequent real-time quantitative PCR Collagen-1, TGF-β1, α-SMA and TIMP-1 mRNA were measured.

Inhibition of Hepasim Compounds on Profibrogenic Gene Expression in Immortalized Hepatic Satellite Cells with Recombinant TGF-β Treatment To examine an additional anti-fibrogenic effect of Hepasim compounds to TGF-β-treated HSC, the inactive HSC cells were seeded at $5 \times 10^5$ per well in 6-well culture plate well and incubated with DMEM medium with 10% FBS for 7 days. The medium was replaced to 1% FBS containing DMEM with various concentrations of Hepasim compounds for additional 72 hours without any profibrogenic agent, and then treated with profibrogenic agent, TGF-β (3 ng/ml) for additional 48 hours. mRNA levels of Collagen-1, TGF-β, α-SMA and TIMP-1 were measured by qRT-PCR.

Cell Proliferation Analysis by BrdU Assay and WST-1 Assay

The Cell Proliferation ELISA, BrdU kit was designed to quantitate cell proliferation bases on the measurement of BrdU incorporation during DNA synthesis in proliferation cells. Briefly, cells (1×104 cells/well) were seeded in 100 µl medium in a 96-well plate (Nunc, Denmark) and cultured for 24 h to allow the cells to attach and then treated with three different concentrations (80 µM, 24 µM and 80 µM) of either Compound A, B, C and D for 24 h, 48 h and 72 h and the plates were incubated in 37° C. After incubation, the culture medium was labeled with 10 µl/well BrdU (Roche Diagnostic Inc.), and the cells were reincubated for addition 16 h at 37° C. Labeling medium was removed using 10 min centrifuge at 200×g and blow dried. Cells were fixed using 200 µl FixDenat solution and incubated for 30 min at room temperature. Removing the FixDenat solution, 100 µl of anti-BrdU-POD was added and incubated for 90 min at room temperature. After the incubation period, microplates were washed three times with PBS buffer and 100 µl substrate solution was added and incubated for 30 min. Stop solution was added (25 µl of 1 M H2SO4) and absorbance of the samples was measured using ELISA reader at 450 nm.

Cell Apoptosis

Apoptosis was detected with a sandwich immunoassay system using a cell death detection ELISA kit (Roche Diagnostic Inc.). Roche's Cell Death Detection ELISA kit qualitatively and quantitatively detects the amount of cleaved DNA/histone complexes (nucleosomes) in a given sample using a sandwich-enzyme-immunoassay-based method. The cells (1×104 cells/well) were seeded in 100 µl medium in a 96-well plate (Nunc, Denmark) and cultured for 24 h to allow the cells to attach and then treated with three different concentrations (8 µM, 24 µM and 80 µM) of either Compound A, B, C and D for 24 h, 48 h and 72 h and the plates were incubated in 37° C. After incubation, the 96 well plates were centrifuged for 10 min at 200×g and removed supernatant and discard, then added 200 µl of lysis buffer per well using multipipetman and incubated 30 min at room temperature, microplates were centrifuged the lysate at 200×g for 10 min. After the centrifuge, 20 µl of the supernatant was transferred into the streptavidin-coated microplate, then added 80 µl of immunoreagent to each well. The microplate was covered with an adhesive foil and incubated on a shaker under gentle shaking for 2 hour at room temperature. After the incubation period, microplates were washed three times with 250-300 µl incubation buffer and 100 µl ABTS solution was added and incubated for 30 min or until color is sufficient for photometric. ABTS Stop solution was added and absorbance of the samples was measured using ELISA reader at 405 nm, reference wavelength at 490 nm.

Result

Improvement of Hepatocyte Damage Parameters.

Figure 7:
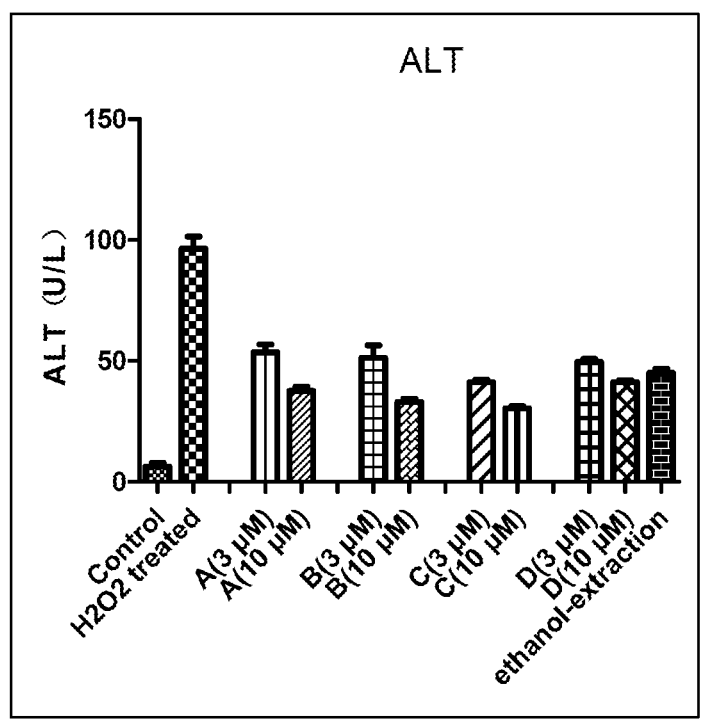
FIG. 7 shows that hepatocyte damage parameters was significantly reduced in cells treated with all compounds and ACM ethanol extract compared to those in the DMSO-treated control cells.

The major parameter about liver damage, Alanine aminotranferease (ALT), was significantly reduced in cells treated with all compounds compared to those in the DMSO-treated control cells. It means significant hepatocyte protection no matter low (3 µM) or high (10 µM) concentration of compound A-D, and the dose-dependent relationship was noted in the alleviation of hepatocyte damage by $H_2O_2$ in all the 4 compounds (FIG. 7).

Figure 8A:
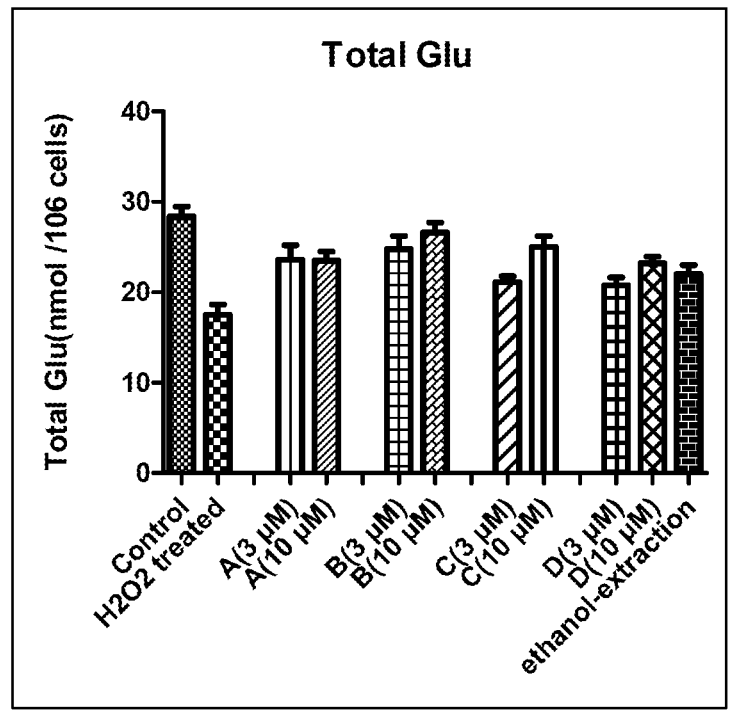
FIGS. 8A and 8B show the Redox status, expressed as Glutathione level and GSH:GSSG ratio as markers for oxidative stress, is significantly improved in cells treated with all compounds and ACM ethanol extract even in lower concentration compared to those in the $H_2O_2$-treated control cells.
Figure 8A:
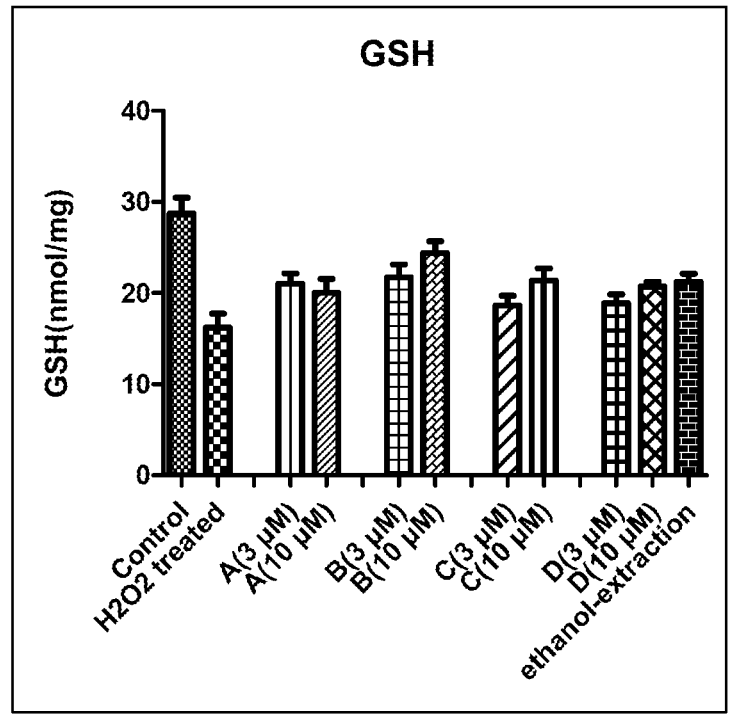
Figure 8B:
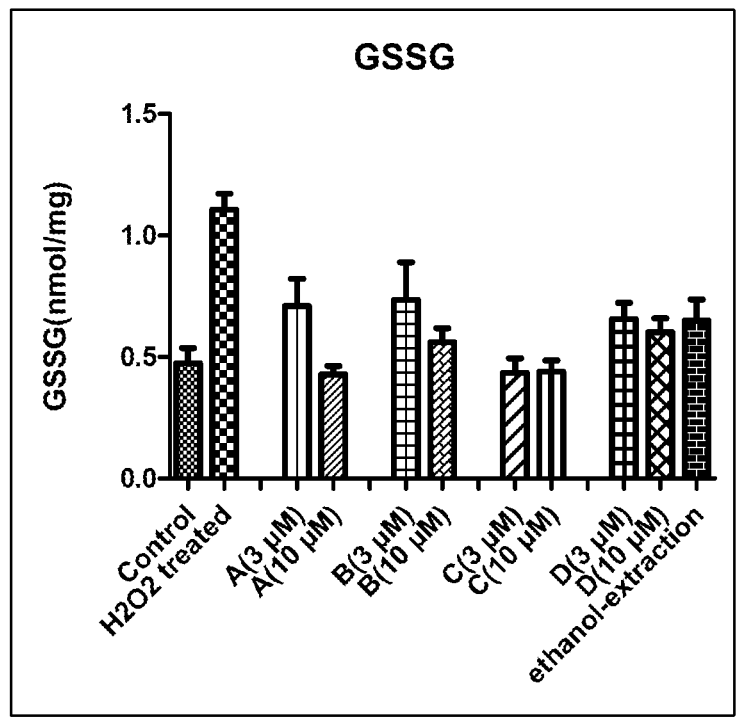
Figure 8B:
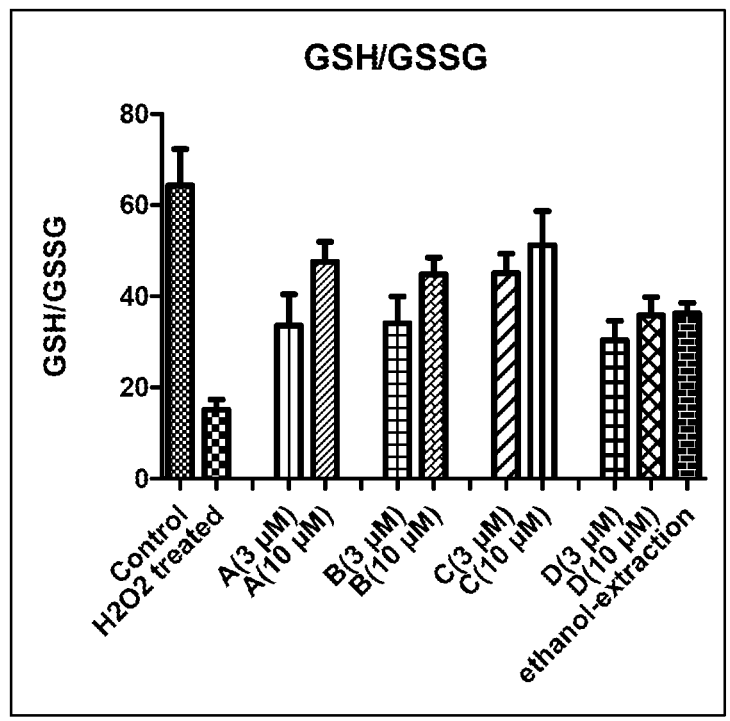

Cellular Reactive Oxygen Species Assay after Hepasim Compounds Treatment:

The Redox status, expressed as Glutathione level and GSH:GSSG ratio as markers for oxidative stress, was significantly improved in cells treated with all compounds even in lower concentration compared to those in the $H_2O_2$-treated control cells. It means significant hepatocyte protection no matter low (3 µM) or high (10 µM) concentration of compound A-D via free radical scavenging (FIGS. 8A and 8B).

Figure 9:
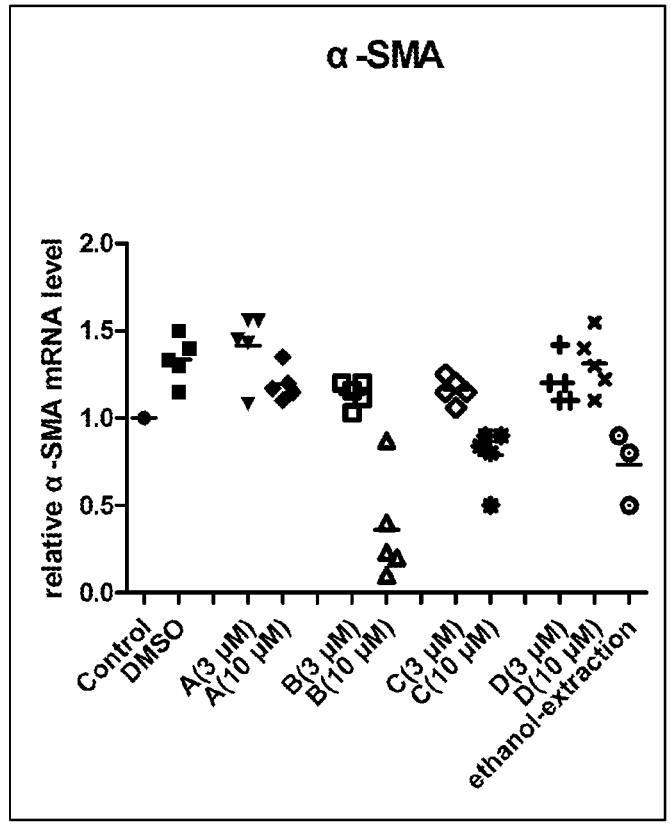
FIG. 9 shows effects of compounds A-D and ACM ethanol extract treatment on profibrogenic genes including αSMA and TIMP-1 expression to primary HSC.
Figure 9:
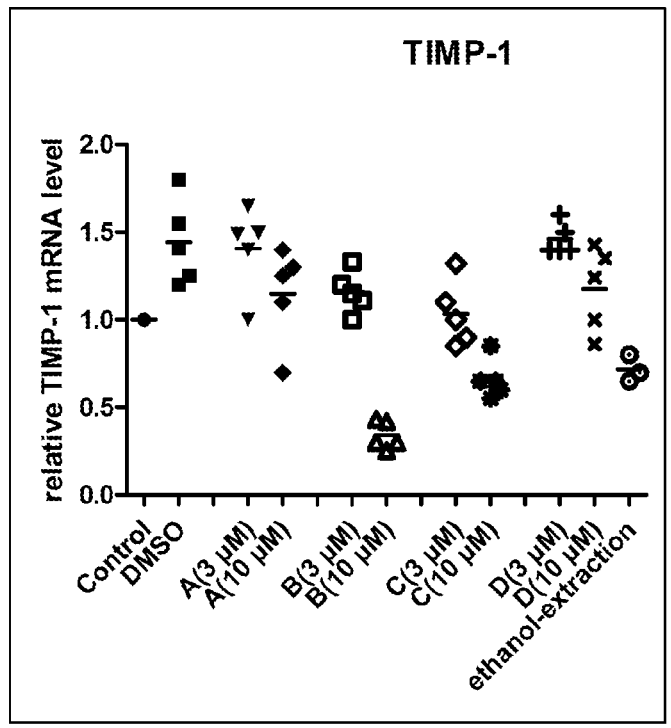

Preventive Effects of Hepasim Compounds on Profibrogenic Gene Expression in Primary Hepatic Satellite Cell:

FIG. 9 shows effects of compounds A-D and ACM ethanol extract treatment on profibrogenic genes including αSMA and TIMP-1 expression to primary HSC. The dose-dependent effect was noted in compounds B and C.

Figure 10:
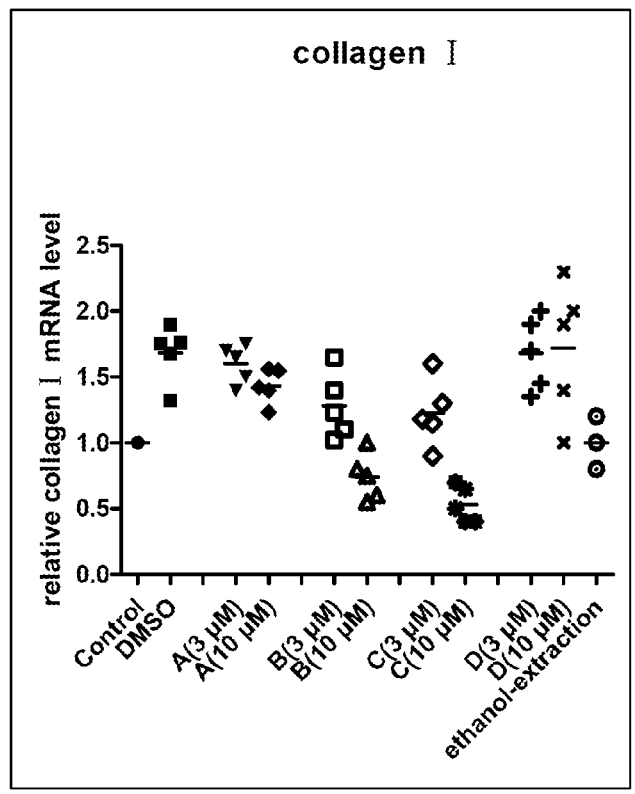
FIG. 10 shows effects of compounds A-D and ACM ethanol extract treatment on profibrogenic genes including Collagen-1 and TGF-β expression in primary HSC.
Figure 10:
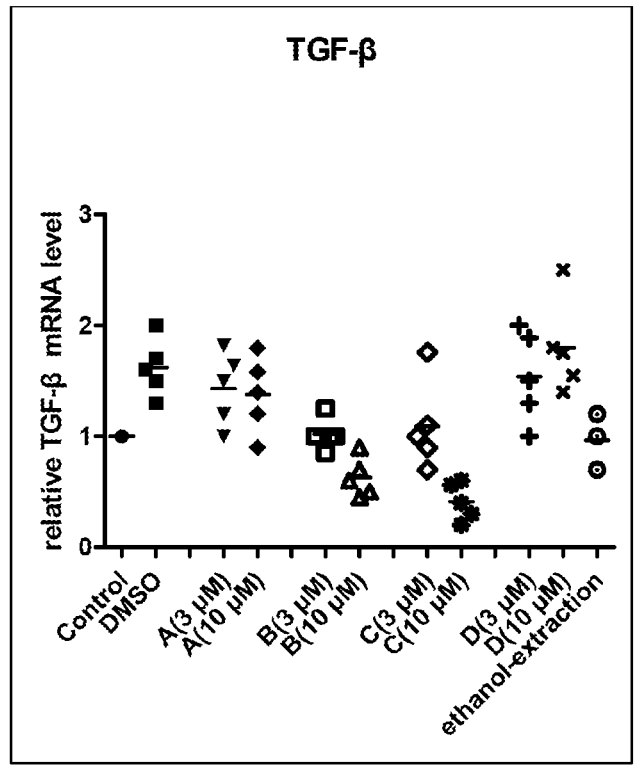
Figure 11:
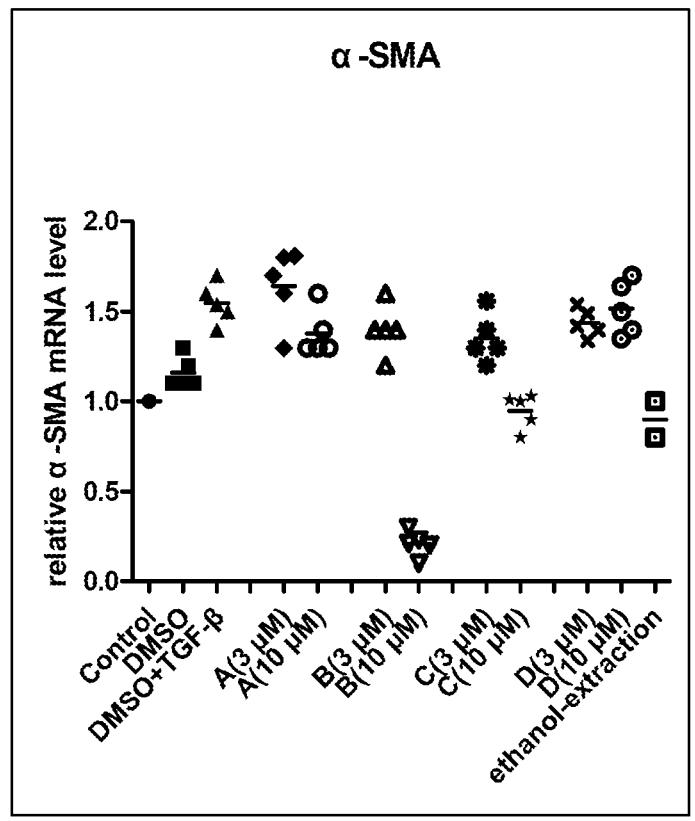
FIG. 11 shows that in comparison to TGFb1-treated immortalized HSC, the preventive effects of compounds A-D and ACM ethanol extract on profibrogenic genes expression including αSMA and TIMP-1.
Figure 11:
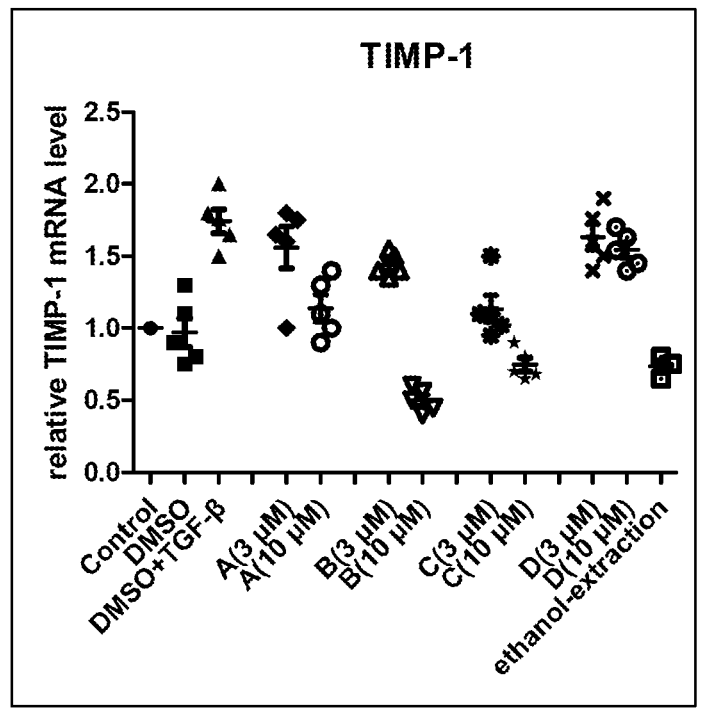

FIG. 10 shows effects of compounds A-D and ACM ethanol extract treatment on profibrogenic genes including Collagen-1 and TGF-β expression in primary HSC. The dose-dependent effect was noted in compounds B and C.
Inhibition of Hepasim Compounds on Profibrogenic Gene Expression in Immortalized Hepatic Satellite Cells with Recombinant TGFb1 Treatment FIG. 11 shows that in comparison to TGFb1-treated immortalized HSC, the preventive effects of compounds A-D and ACM ethanol extract on profibrogenic genes expression including αSMA and TIMP-1. The dose-dependent effect was noted in compounds B and C.

Figure 12:
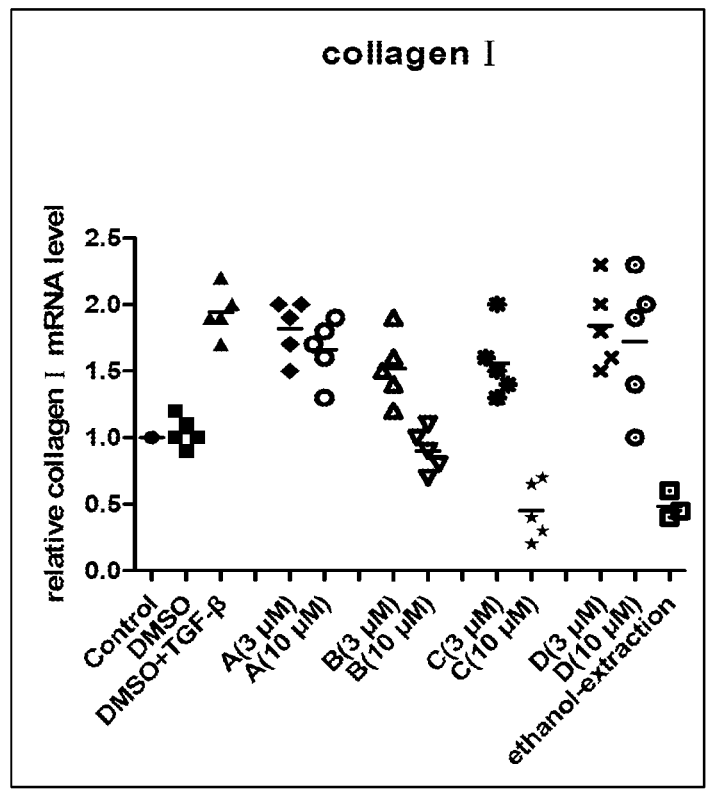
FIG. 12 shows that in comparison to TGFb1-treated immortalized HSC, the preventive effects of compounds A-D and ACM ethanol extract on profibrogenic genes expression including Collagen-1 and TGF-β.
Figure 12:
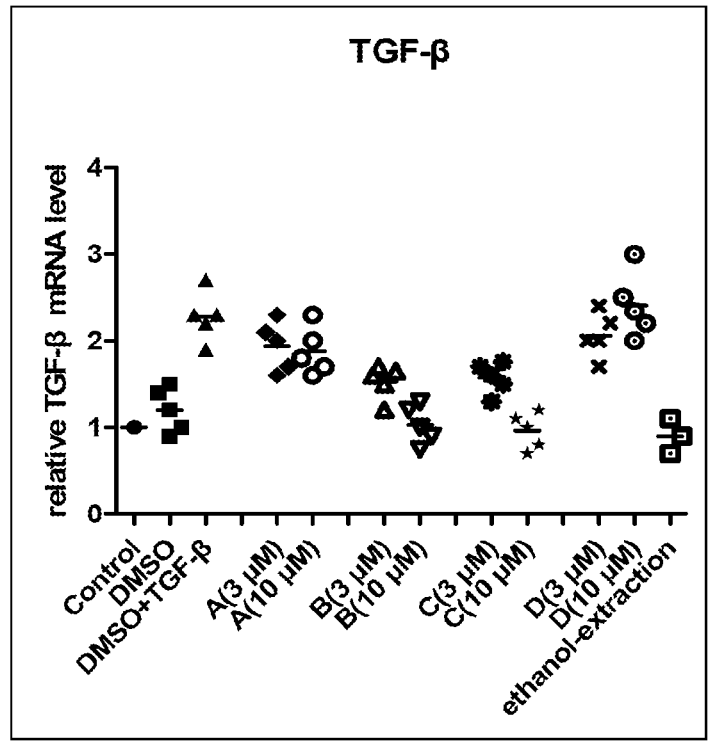
Figure 13:
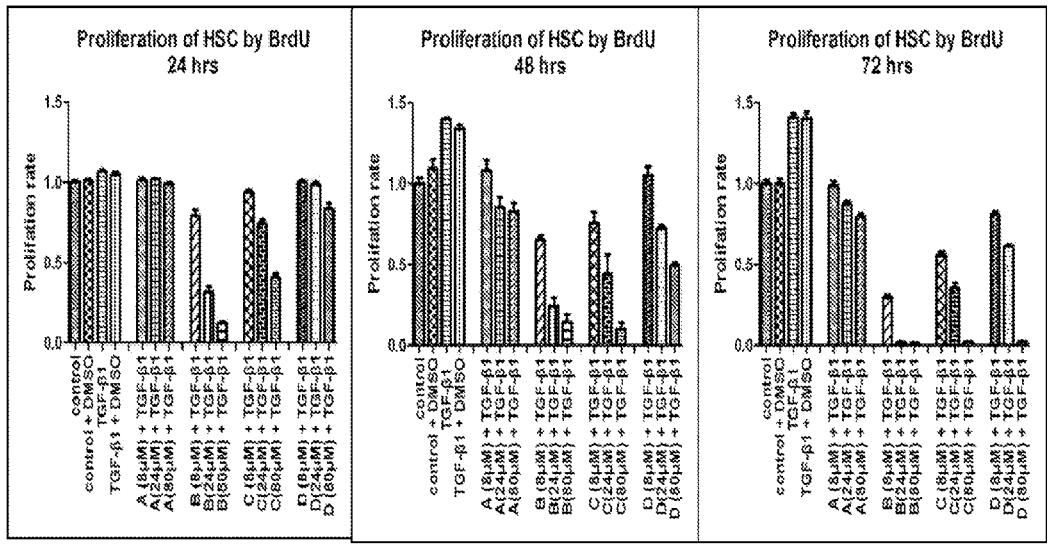
FIG. 13 shows comparison of the differences in HSC proliferation presented by BrdU assay and apoptosis by cell death detection assay to assess the antifibrotic effects of higher concentration of hepasims.
Figure 13:
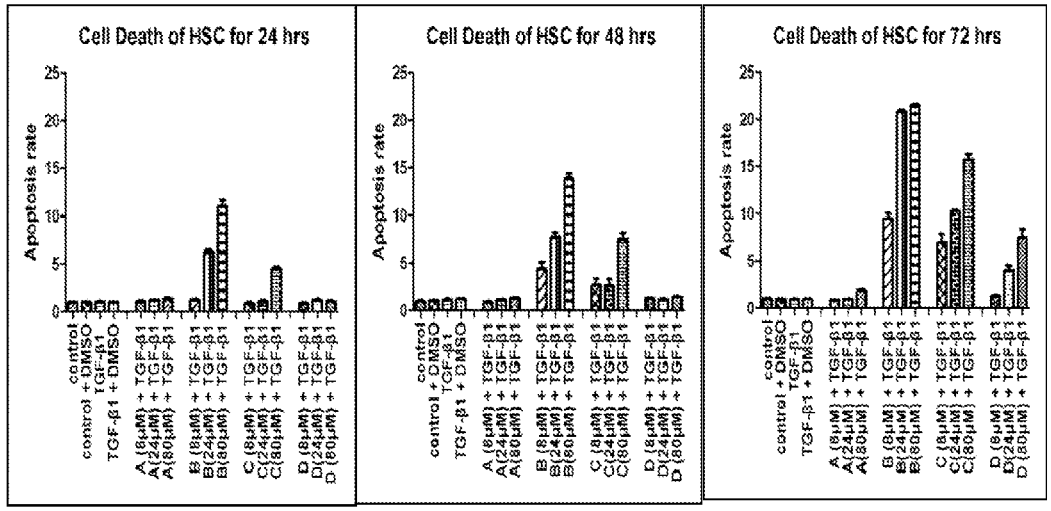

FIG. 12 shows that in comparison to TGFb1-treated immortalized HSC, the preventive effects of compounds A-D and ACM ethanol extract on profibrogenic genes expression including Collagen-1 and TGF-β. The dose-dependent effect was noted in compounds B and C.
The Therapeutic Effect of Higher Concentrated Hepasims on HSC To assess the antifibrotic effects of higher concentration of hepasims (24-80 μM), a comparison of the differences in HSC proliferation was presented by BrdU assay and apoptosis by cell death detection assay. The results showed markedly proliferation inhibition and apoptosis of HSC in the subgroups treated by compound B and C, and the compound D showed the same but delayed (72 hours later) effect in highest concentration (80 μM) (FIG. 13). Compound B showed the most potent effect compared to other compounds.
Conclusion The summary of cellular study indicated that all compounds have significant protective effects on hepatocyte damage. Compound B and C also exhibited an anti-fibrosis effect on immortalized HSC in response to TGF-β and primary HSC. According to all in vitro experiments, compound B and C was the candidate to further determine anti-fibrosis experiment in vivo.

Example 3

Hepasims for Liver Fibrosis—Animal Study for the Anti-Fibrotic Effect of Compound B and C Compound B and C showed most potent anti-fibrotic effect in cellular study. The further animal study for compound B and C was designed to reappraisal the clinical potency of the two compounds for liver cirrhosis.
Method
Cirrhotic Animal Model:

Male Wistar rats (150-180 g) at 7 weeks of age were obtained from the Animal Center of National Taiwan University. The rats were housed in standard conditions, and all the experiments were conducted in accordance with the "Guide for the Care and Use of Laboratory Animals" prepared by the Institutional Animal Care and Use Committee of National Taiwan University. The rats were given DEN solution daily (Sigma, St Louis, Mo.) as the sole source of drinking water for 9 weeks, followed by 2 weeks of regular water. It starts with 100 ppm (vol/vol) in the first week. The average BW of the animals was measured once a week, and the concentration of DEN in their drinking water was adjusted in proportion to the BW each week relative to that of the first week.

Preparation of Hepasim Compounds:

As described above in Example 2, hepasim compounds (i.e. compounds A-E) were equal to compounds 1-5 disclosed in U.S. Pat. No. 7,109,232. The methods for preparing hepasim compounds were the same as those disclosed in U.S. Pat. No. 7,109,232.

Hepasim compounds B and C were extracted from ACM. Finely compounds B (7 mg/kg), C (14 mg/kg) and 320 mg/kg ACM were prepared with sterile distilled water and fed to rats respectively through a gastric tube every day from $5^{th}$ to $11^{th}$ week. Some of the animals were sacrificed in $11^{th}$ week and their livers were sampled for pathologic examination and gene expression assay.
Biochemical Analysis of Serum Samples of 1 ml blood were gathered from the retro-orbital plexus of each mouse and immediately centrifuged at 1300×g at 4° C., plasma was kept at −20° C. for liver function tests. Alanine aminotranferease (ALT), aspartate aminotransferase (AST), total bilirubin and Gamma-glutamyl transpeptidase (γ-GT) levels were determined using commercial enzymatic kits with a colorimetric analyzer (Dri-Chem 3000, Fuji Photo Film Co, Tokyo, Japan).
Measurement of Hydroxyproline Content in the Liver.

Liver collagen content was determined from the tumor-free liver samples by quantifying the levels of hydroxyproline. In brief, liver sample (between 15 and 25 mg) in an Eppendorf tube containing 20 mL of 6 N HCl was carefully ground using a pestle. Additional 6 N HCl was then added to make a total volume of 30 mL/mg tissue and in a way to wash down the residual tissue fragments on the pestle. The ground tissue in HCl was hydrolyzed at 120∞C for 16 h. After brief cooling on ice and centrifugation at 8000 g for 10 min, the supernatant was removed to a new tube; the lost volume by evaporation was replenished by water. Equal volume of 6 N NaOH was added and mixed, and the solution was adjusted to pH 4-9 using litmus paper. Forty microliters of the neutralized sample solution was removed to a 96-well ELISA plate and oxidized in each well with a solution containing 5 mL of 7% Chloramine T (Sigma, St Louis, Mo., USA) and 20 mL of acetate/citrate buffer (57 g sodium acetate.3H2O, 37.5 g trisodium citrate.2H2O, 5.5 g citric acid.H2O, 385 mL isopropanol, and dissolved in $H_2O$ to a final volume of 1 L). Thereafter 150 mL of Ehrlich's solution was added. The Ehrlich's solution was prepared by dissolving 2 g of pdimethylamino-benzaldehyde (Sigma) in 3 mL of 60% HClO4 (Merck, Darmstadt, Germany) and then mixed with 9 mL of isoprapanol. The final mixture was incubated at 60° C. for 35 min and then at room temperature for 10 min, and the absorbance was determined at 560 nm. Standard solutions containing 100, 80, 60, 40, 20 and 0 mg/mL of authentic 4-hydroxy-L-proline (Sigma) were treated likewise. The standard curve was linear in this range (r=0.98). The value of the liver hydroxyproline level was expressed as mg/g wet tissue.
Immunohistochemistry and Histological Staining.

Liver samples were fixed in formalin and embedded in paraffin for Sirius red staining. For detecting hepatic fibrosis, liver sections were stained for 1 hour with 0.1% (wt/vol) Sirius red (Sigma, St Louis, Mo.) in a saturated aqueous solution of picric acid (Wako, Osaka, Japan). After staining, the slides were rinsed with two changes of acidified water [0.5% (wt/wt) glacial acetic acid in H2O], and then dehydrated in three changes of 100% ethanol. The slides were cleared in xylene, mounted in a resinous medium, and then observed under a light microscope. Sirius red-positive areas were measured using the Digital Camera System HC-2500 and Image-Pro Plus.

Quantitative Real-Time Reverse Transcription Polymerase Chain Reaction (RT-PCR) Analysis of Collagen Expression and Oxidative Stress Sample tissues of rat livers were measured about 0.5×0.5 cm in area. Each of tissue was homogenized in 1 mL of TRIzol buffer (Invitrogen, Carlsbad, Calif., USA) with a motorized pestle, and then mixed with 0.5 mL chloroform/ isoamyl alcohol (24:1), and was centrifuged at 12,000×g for 10 min at 4° C. The supernatant was transferred to a fresh tube, and isopropanol was added, mix well and stored at −80° C. overnight. The reaction mixture was centrifuged at 12,000×g for 30 min at 4° C. to produce a rude RNA pallet, the pellet was washed with 70% ethanol and air-dried. The concentrations of total RNA were measured by absorbance at 260 nm using a NanoDrop ND-1000 (NanoDrop, USA). Reverse transcription reaction was performed using a commercially available set of High Capacity RNA-to-cDNA Kit (Applied Biosystems, USA). cDNA was prepared from 2 µg of total RNA per 20 µl reaction, according to the manufacturer's instructions—37° C. for 60 minutes, 95° C. for 5 minutes, and hold at 4° C. The resulting cDNA was to a final concentration of 100 ng/µl and constituted a matrix in further experiments. Amplification and detection the gene expression by real-time PCR were performed using StepOne plus Real-time PCR System (Applied Biosystems, USA). Samples were assayed in a 10 µl reaction mixture containing 2 µl of template DNA, 5 µl of 2× TaqMan PCR Master Mix (Applied Biosystems, Life Technologies, Foster City, Calif., USA), 0.5 µl of 20× assay mix containing probe, forward and reverse primer (Applied Biosystems, Life Technologies, Foster City, Calif., USA), whereby qPCR targets with the following information were used: (a) Rat α-SMA, Assay ID Rn01759928_g1, (b) Rat TIMP-1, Assay ID Rn00587558_m1, (c) Rat TGF-β1, Assay ID Rn00572010 ml, (d) Rat Collagen I, Assay ID Rn 01463838_m1, (e) Rat CuZnSOD, Assay ID Rn00566938_m1, (f) Rat MnSOD, Assay ID Rn00690587_g1, (g) Rat Catalase, Assay ID Rn00560930_m1, (h) Rat Glutathione peroxidase, Assay ID Rn00577994_g1, (i) Rat NADPH oxidase, Assay ID Rn00585380_m1 and (j) Rat GAPDH, Assay ID Rn1462662_g1. To control variation in mRNA concentration, all results were normalized to the housekeeping gene, GAPDH. The cycling conditions used were as follows: 50° C. for 2 min, 95° C. for 10 min followed by 40 cycles of 95° C. for 15 s and 60° C. for 1 min each.

Result

Improvement of Hepatic Damage Parameters

Figure 14:
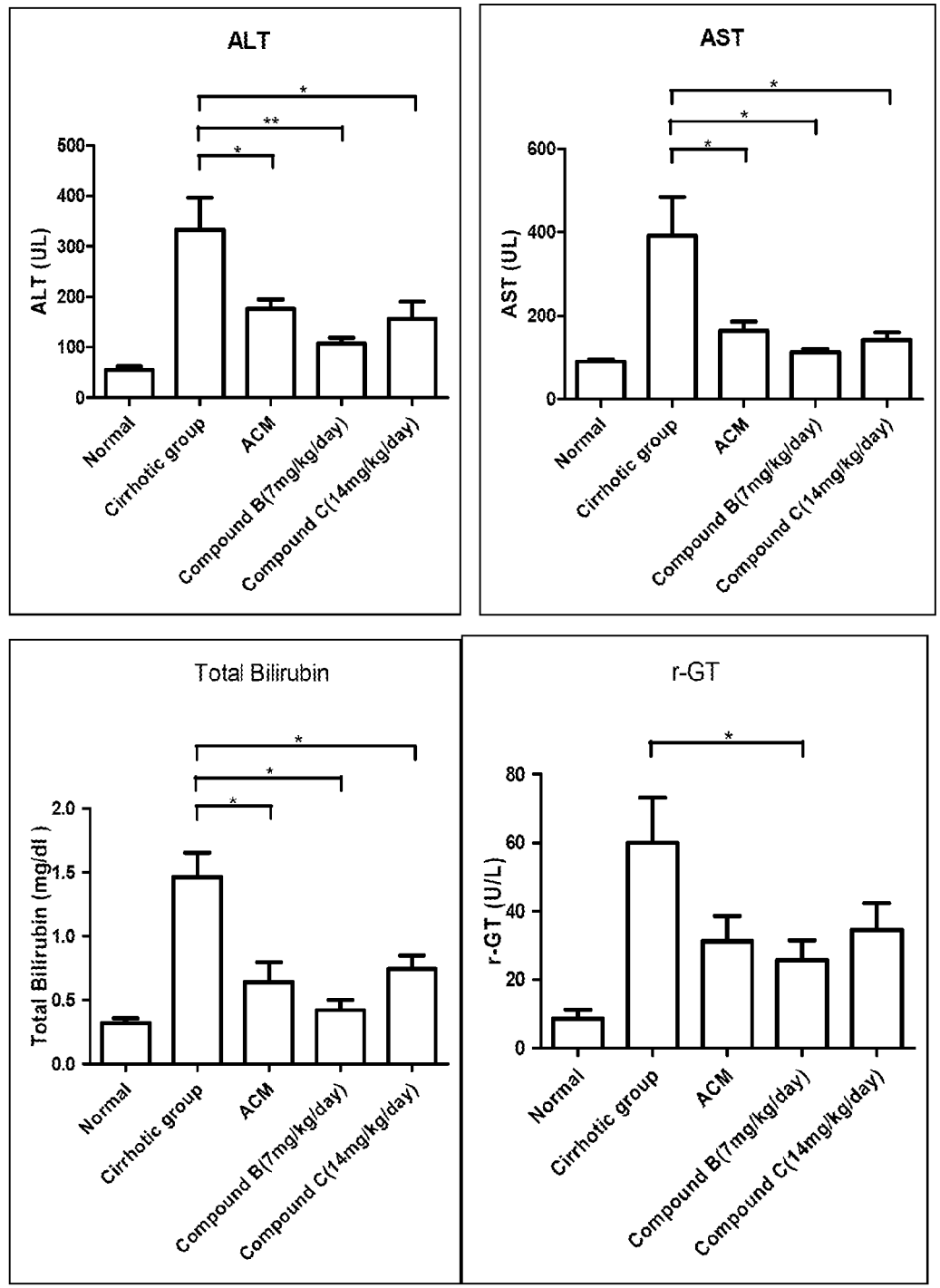
FIG. 14 shows that serum parameters about liver damage including Alanine aminotranferease (ALT), aspartate aminotransferase (AST), total bilirubin and Gamma-glutamyl transpeptidase (γ-GT) levels all showed significantly reduced in the animals fed 320 mg/kg/day ACM and both compounds compared to control group.

At the end of the experiment, the serum parameters about liver damage including Alanine aminotranferease (ALT), aspartate aminotransferase (AST), total bilirubin and Gamma-glutamyl transpeptidase (γ-GT) levels all showed significantly reduced in the animals fed 320 mg/kg/day ACM and both compounds compared to control group (FIG. 14). It means significant hepatocyte protection by compounds B and C.

Amelioration of Liver Fibrosis

Figure 15:
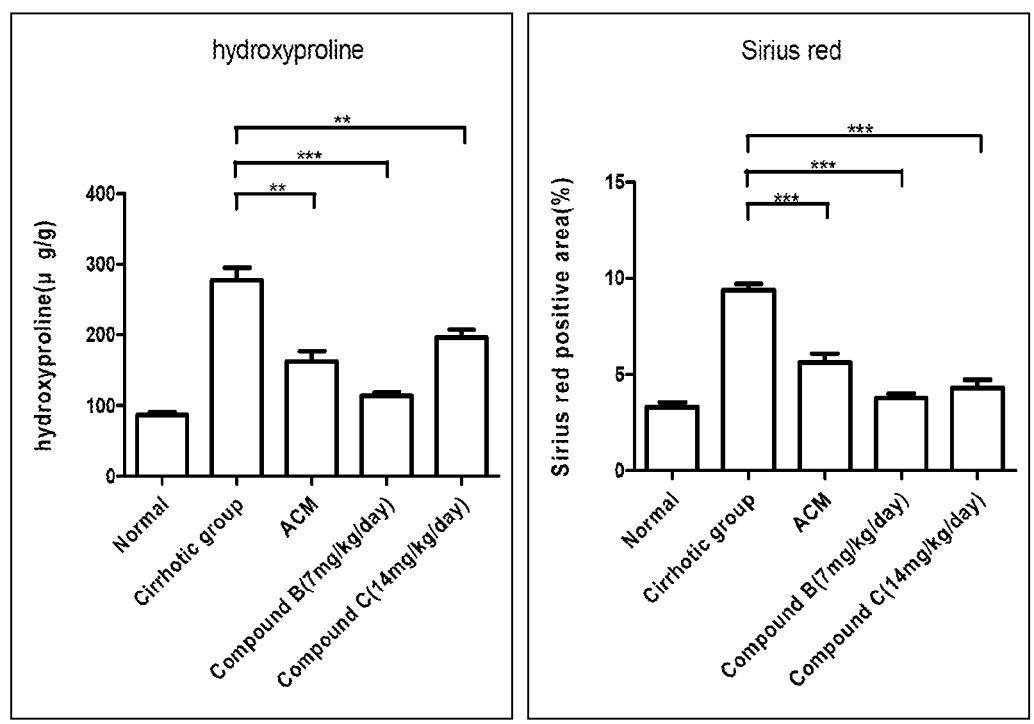
FIG. 15 shows comparison of the differences in hydroxyproline levels between the livers in treatment groups and control group and in microscopically Sirius red-positive areas also to assess the antifibrotic effects of compounds B and C.

To assess the antifibrotic effects of compound B and C, a comparison of the differences in hydroxyproline levels between the livers in treatment groups and control group and in microscopically Sirius red-positive areas also. The results showed markedly ameliorated liver cirrhosis in animals fed ACM and compounds B and C (FIG. 15).

Reduce of Pre-Fibrotic Gene Expression

Figure 16:
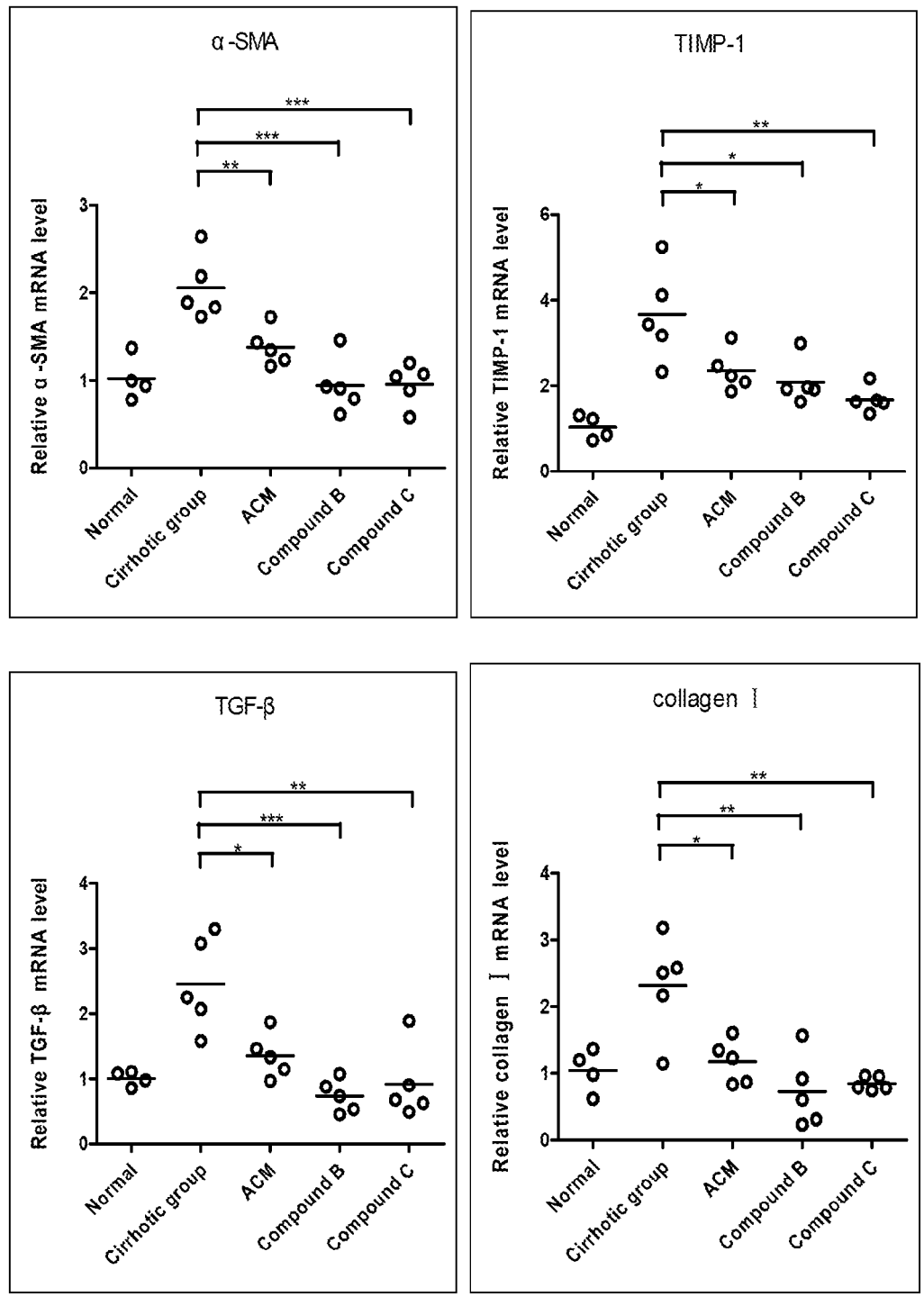
FIG. 16 shows that expressions of pre-fibrotic genes including α-SMA, TIMP, Collagen type I and TGF-β1 were reduced significantly in the animals fed ACM, compounds B and C.

The expressions of pre-fibrotic genes including α-SMA, TIMP, Collagen type I and TGF-β1 were reduced significantly in the animals fed ACM, compounds B and C (FIG. 16).

Decrease of Oxidative Stress

Figure 17A:
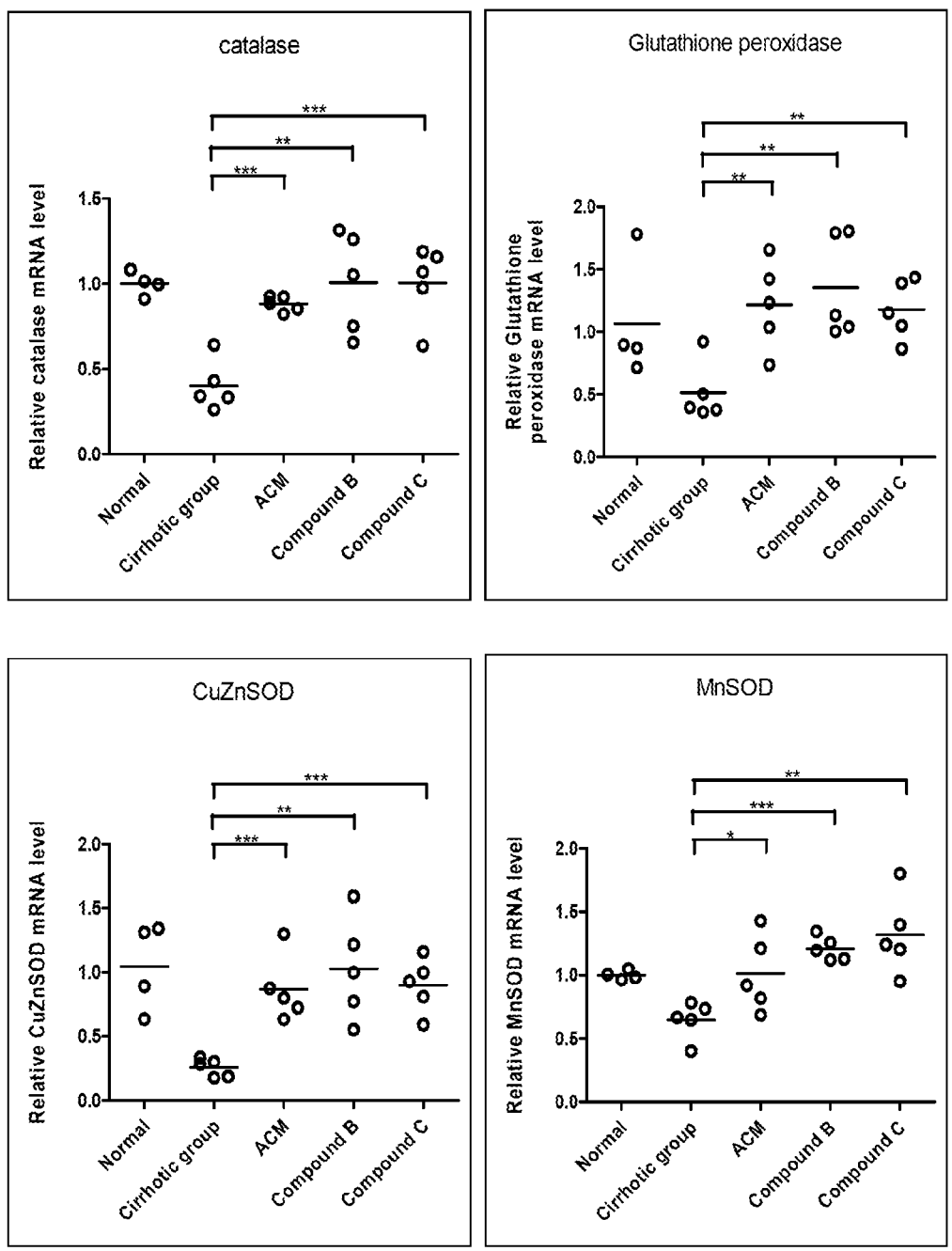
FIGS. 17A and 17B show the gene expression of anti-oxidant enzyme including CuZnSOD, MnSOD, Catalase and Glutathione peroxidase were up-regulated significantly in the animals fed with ACM, compound B and C, and the gene expression of NADPH oxidase, a main enzyme to generate reactive oxidative species (ROS), was down-regulated significantly.
Figure 17B:
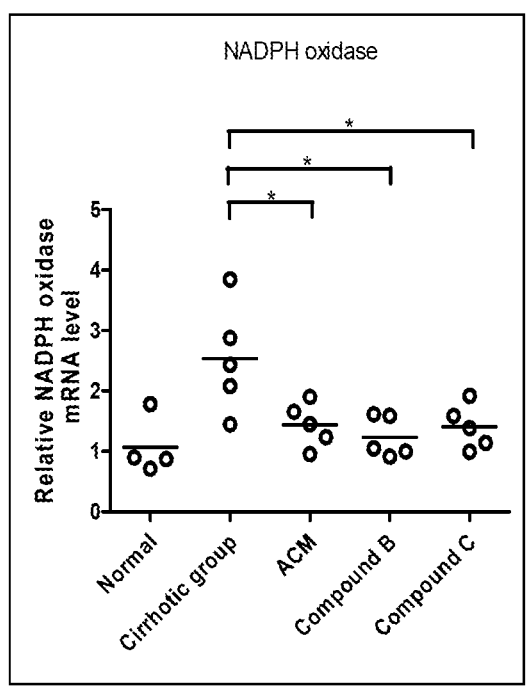

After treatment, the gene expression of anti-oxidant enzyme including CuZnSOD, MnSOD, Catalase and Glutathione peroxidase were up-regulated significantly in the animals fed with ACM, compound B and C, and the gene expression of NADPH oxidase, a main enzyme to generate reactive oxidative species (ROS), was down-regulated significantly (FIGS. 17A and 17B).

Figure 18:
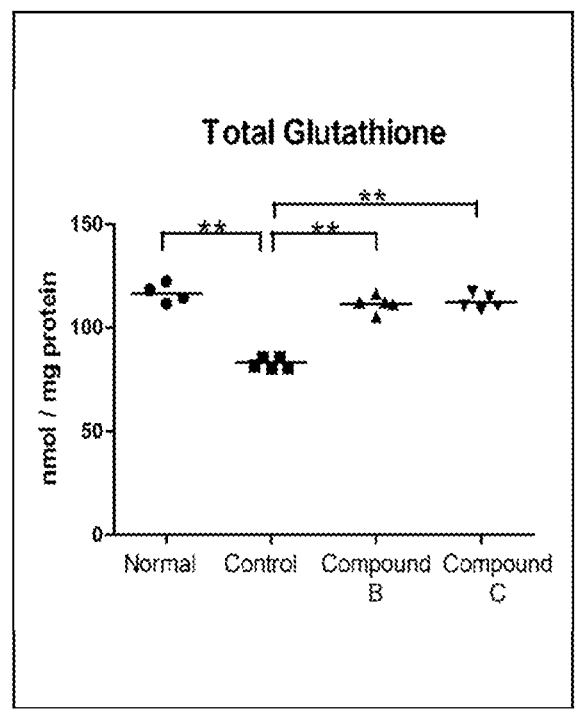
FIG. 18 shows the Redox status, expressed as Glutathione level and GSH:GSSG ratio as markers for oxidative stress, was significantly improved in the cirrhotic animals treated with compounds B and C.
Figure 18:
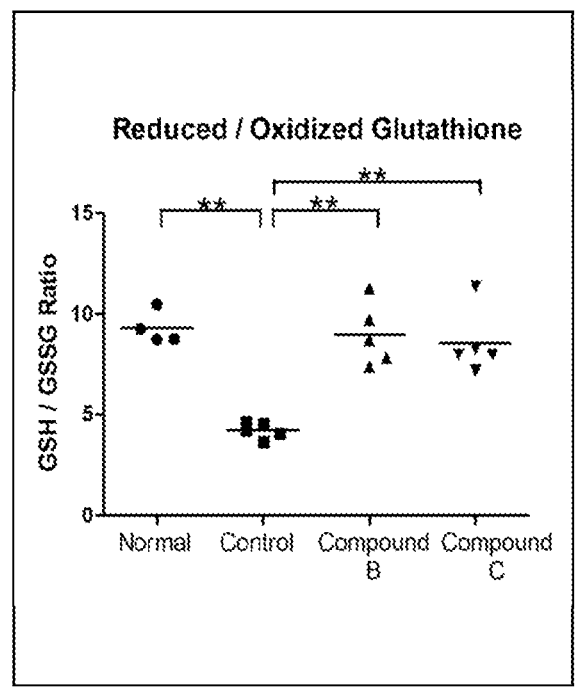

The Redox status, expressed as Glutathione level and GSH:GSSG ratio as markers for oxidative stress, was significantly improved in the cirrhotic animals treated with compounds B and C (FIG. 18). It means the treatment of compounds B and C can decrease oxidative stress accompanied with liver fibrosis significantly.

Conclusion

The summary of animal study indicated that compounds B and C can exhibit an anti-fibrosis effect on cirrhotic animals, and as good free radical scanvengers, compounds B and C can decrease the oxidative stress in liver also.

Example 4

Hepasims for Skin Damage—Cellular Study for Hepasims

This experiment was designed to verify the hypothesis that the anti-fibrotic and anti-oxidant effect of ACM results from hepasims. The possible role of hepasims in inhibiting scar overformation and in the treatment of physical damage to skin such as redox reaction and UV exposure was studied. In this Example, dermal fibroblasts CG1639 and skin keratinocyte were used for studying hepasims' effect on skin. Dermal fibroblasts are cells that live within the dermis layer of skin which are responsible for generating connective tissue and allowing the skin to recover from injury.

Method

Cells

The dermal fibroblast cell line CG1639 was obtained from the BCRC (Bioresource Collection and Research Center) and cultured in Dulbecco's modified Eagle media (DMEM, Gibco by Invitrogen) with 1% antibiotic antimycotic (Gibco by Invitrogen) and 15% fetal bovine serum (Gibco by Invitrogen). The fetal rat skin keratinocyte, FRSK cell line was obtained from the Japan HSRRB (Health Science Research Resources Bank) and cultured in Eagle's minimal essential media (MEM, Gibco by Invitrogen) supplemented with 10% fetal bovine serum (FBS) (Gibco by Invitrogen) and 1% antibiotic antimycotic (Gibco by Invitrogen). B16F10 cells, a murine melanoma cell line, were purchased from American Type Culture Collection (ATCC, Rockville, Md., USA) and was cultured in Eagle's Minimum Essential Medium (MEM; Sigma, St. Louis, Mo.) supplemented with 10% fetal bovine serum (FBS; HyClone Lab. Inc., Logan, Utah), 0.02% antibiotic-antimycotic liquid (penicillin, 10 000 U $mL^{-1}$; streptomycin, 10 000 µg $mL^{-1}$ and amphotericin B, 25 µg $mL^{-1}$; Invitrogen, Carlsbad, Calif.).

The three cell lines were cultured at 37° C. in a humidified atmosphere containing 5% CO2.

Preparation of Hepasim Compounds:

As described above in Example 2, hepasim compounds (i.e. compounds A-E) were equal to compounds 1-5 disclosed in U.S. Pat. No. 7,109,232. The methods for preparing hepasim compounds were the same as those disclosed in U.S. Pat. No. 7,109,232.

It was noted that in the following experiments, "compound D" referred to a racemic mixture of compound D and compound E, and in which the ratio of compound D to compound E was preferably 1:1~2:1. In an embodiment, the ratio of compound D to compound E is about 1.62:1.

Effects of Hepasim Compounds on Melanoma Cells and Keratocytes with Ultraviolet Irradiation:

To investigate the induction of melanogenesis and the oxidative stress by direct UV irradiation, melanoma cells and keratocytes were irradiated with 8 J cm$^{-2}$ of UVA (FL15BLB, 352 nm, 15 W; Toshiba, Tokyo, Japan) and 10 mJ cm$^{-2}$ of UVB (G15T8E, 306 nm, 15 W; Sankyo Denki, Tokyo, Japan) in a HANKS' balanced salt solution (Sigma). The UV intensity was measured by using a Model UVX Digital Radiometer (UVP Inc., Upland, Calif.).

B16F10 and FRSK cells were exposed to Hepasim compounds A-D by two different concentrations (3 or 10 μM) for 72 hrs prior to UVA irradiation. DMEM was replaced with phosphate buffered saline (PBS) to avoid generation of medium-derived toxic photoproducts prior to UV irradiation. Cells were collected 24 hrs after UVA irradiation and assayed. For preparation of cell lysate, the harvested cells were pelleted by centrifugation and lysed in lysis buffer containing 50 mM Tris-HCl, 10 mM ethylene diaminetetraacetic acid (EDTA), 1% (v/v) Tri-ton X-100, phenylmethylsulfonyl fluoride (PMSF) (100 mg/ml) and pepstatin A (1 mg/ml) in DMSO and leupeptin (1 mg/ml) in H2O, pH 6.8. The cells were centrifuged at 10,000 rpm for 10 min and the total cell lysate was collected and stored at −80° C.

Assay of Melanin Content

In order to measure the melanin contents, B16F10 cells were sonicated on ice and the mixture was centrifuged (25 000 g, 10 min, 4° C.). The supernatant was transferred, and pellets were dissolved in 0.85 N KOH at 60° C. for 20 min. Standard melanin (Sigma) was incubated in parallel. Spectrophotometric analysis of melanin content was then performed at an absorbance of 405 nm Tyrosinase Activity Assay The rate of L-DOPA oxidation was measured to assess cellular tyrosinase activity in B16F10 cells exposed to UV. The assay was performed as below described, 20 mM L-DOPA used as the substrates was added to each lysate in a 96-well plate and absorbance of dopachrome formation was measured spectrophotometrically at 475 nm every 10 min for 1 h at 37° C. by a spectrophotometer. The tyrosinase activity was calculated by comparison to a standard curve using tyrosinase (2034 U/mg) and was expressed as unit/mg protein. The data are expressed as a percentage of the tyrosinase activity (unit/mg protein) of non-irradiated and untreated control cells (100%).

Cellular Reactive Oxygen Species Assay of Keratocytes with Ultraviolet Irradiation A commercially available kit (# K264-100, BioVision) was used to measure glutathione (GSH), and oxidized glutathione (GSSG). The GSH/GSSG ratio was determined from these data. The assay was conducted with several modifications to the manufacturer's directions. Briefly, cellular pellet (~10 mg) was homogenized immediately, and take 60 μl of each sample to a prechilled tube containing Perchloric Acid and centrifuged at 13,000×g for 2 min, collect supernatant and stored at −80° C. until analyzed. The assay was conducted as described by the manufacturer. Briefly, cold 3N KOH was added to each sample mixed, and centrifuged at 13,000×g for 10 min. Ten microliters of each sample and the appropriate buffer and 90 μl of Assay Buffer to detect GSH and 10 μl of glutathione reductase were mixed to detect total glutathione and 10 μl of GSH Quencher to detect GSSG and incubated at room temperature for 40 min and the absorbance of each sample was read at 340/420 nm for 3 min. The protein concentration for each sample was determined via a DC protein concentration assay (Bio-Rad). Signals from each sample were normalized to the corresponding protein content of that sample.

RNA Extraction of Cell and Quantitative Reverse Transcription-Polymerase Chain Reaction (RT-PCR)

Reverse transcription reaction was performed using a commercially available set of High Capacity RNA-to-cDNA Kit (Applied Biosystems, USA). cDNA was prepared from 2 μg of total RNA per 20 μl reaction, according to the manufacturer's instructions—37° C. for 60 minutes, 95° C. for 5 minutes, and hold at 4° C. The resulting cDNA was to a final concentration of 100 ng/μl and constituted a matrix in further experiments.

Amplification and detection the gene expression by real-time PCR were performed using StepOne plus Real-time PCR System (Applied Biosystems, USA). Samples were assayed in a 10 μl reaction mixture containing 2 μl of template DNA, 5 μl of 2× TaqMan PCR Master Mix (Applied Biosystems, Life Technologies, Foster City, Calif., USA), 0.5 μl of 20× assay mix containing probe, forward and reverse primer (Applied Biosystems, Life Technologies, Foster City, Calif., USA), whereby qPCR targets with the following information were used: (a) α-SMA, Assay ID Rn01759928_g1, (b) TIMP-1, Assay ID Rn00587558_m1, (c) TGF-β1, Assay ID Rn00572010_m1, (d) Collagen I, Assay ID Rn 01463838_m1, (e) GAPDH, Assay ID Rn1462662_g1. To control variation in mRNA concentration, all results were normalized to the housekeeping gene, GAPDH. Relative quantitation was performed using the comparative ΔΔCt method according to the manufacturer's instructions. The cycling conditions used were as follows: 50° C. for 2 min, 95° C. for 10 min followed by 40 cycles of 95° C. for 15 s and 60° C. for 1 min each.

Preventive Effects of Hepasim Compounds on Profibrogenic Gene Expression in Dermal Fibroblast Cell Lines:

Dermal fibroblast, CG1639 cells, were exposed to Hepasim compounds by two different concentrations for 72 hrs. Then, RNA was extracted and subsequent real-time quantitative PCR Collagen-1, TGF-β1, α-SMA and TIMP-1 mRNA were measured.

Result

Hepasim Inhibited Melanogenesis after UV Exposure.

To determine the antimelanogenic effects of Hepasim, the effect of UV irradiation on melanin content in B16F10 cells was investigated. Non-UV irradiated B16F10 cells showed melanin levels of 7.4±0.3 μg/mg protein, A substantial increase in melanin production of 33.80±4.6% (P<0.001) in B16F10 cells irradiated with the UV source. The presence of 10 μM Hepasim compounds B and C prior to UV irradiation resulted in suppression of melanin formation (compound B: 29.40±4.3%; compound C: 28.92±5.3%), and melanoma cells treated by compounds A and D also showed decreased melanin content (compound A: 23.25±5.5%, P=0.04; compound D: 26.32±2.3%, P=0.037).

It was further investigated whether the antimelanogenic effects were attributed to its inhibitory effects on tyrosinase, a rate-limiting step enzyme for melanin synthesis. B16F10 cells were observed to have 3.0±0.5 U/mg protein in non-UV-irradiated control cells. UV irradiation was demonstrated to cause 52.55±4.36% (P<0.001) increase in tyrosinase activity in B16F10 cells. The treatment of compound A-D at concentrations of 3 and 10 μM led to a concentration-dependent protection against UV-mediated tyrosinase activation B16F10 cells (3 μM compound A: 43.50±3.5%, 10 μM compound A: 26.75±2.3%; 3 μM compound B: 51.65±4.6%, 10 μM compound B: 42.32±6.7%; 3 μM compound C: 48.55±3.7%, 10 μM compound C: 40.55±3.9%; 3 μM compound D: 38.5±4.5%, 10 μM compound D: 29.25±2.6%)

Cellular Reactive Oxygen Species Assay after Hepasim Compounds Treatment

Figure 19:
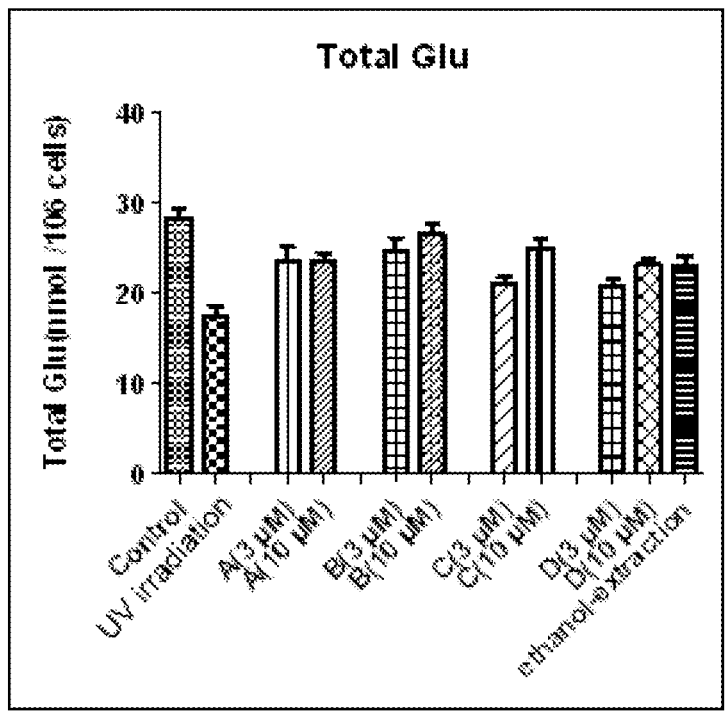
FIG. 19 shows the Redox status, expressed as Glutathione level and GSH:GSSG ratio as markers for oxidative stress, was significantly improved in cells treated with all compounds and ACM ethanol extract even in lower concentration compared to those in the UV-exposed control cells.
Figure 19:
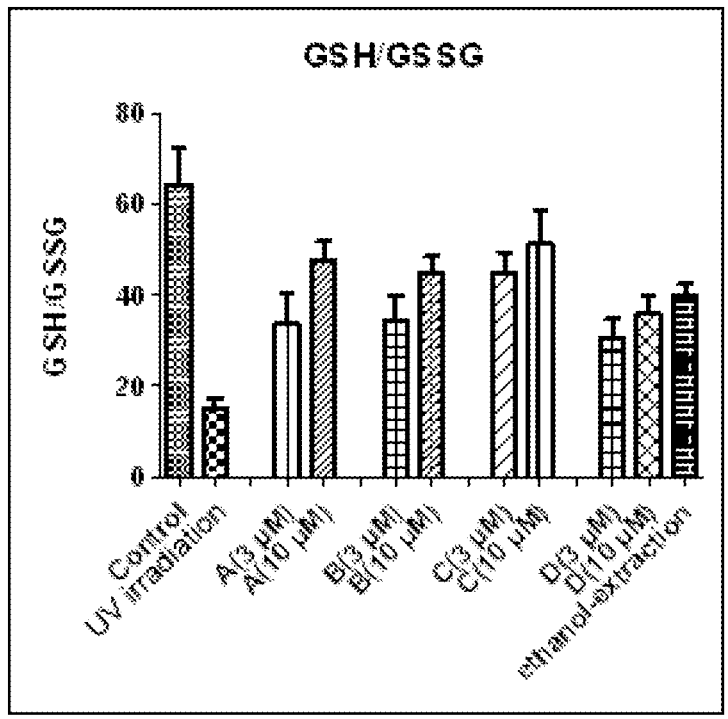

The Redox status, expressed as Glutathione level and GSH:GSSG ratio as markers for oxidative stress, was significantly improved in cells treated with all compounds and ACM ethanol extract even in lower concentration compared to those in the UV-exposed control cells (FIG. 19). It means significant keratocyte protection no matter low (3 μM) or high (1004) concentration of compounds A-D via free radical scavenging.

Figure 20:
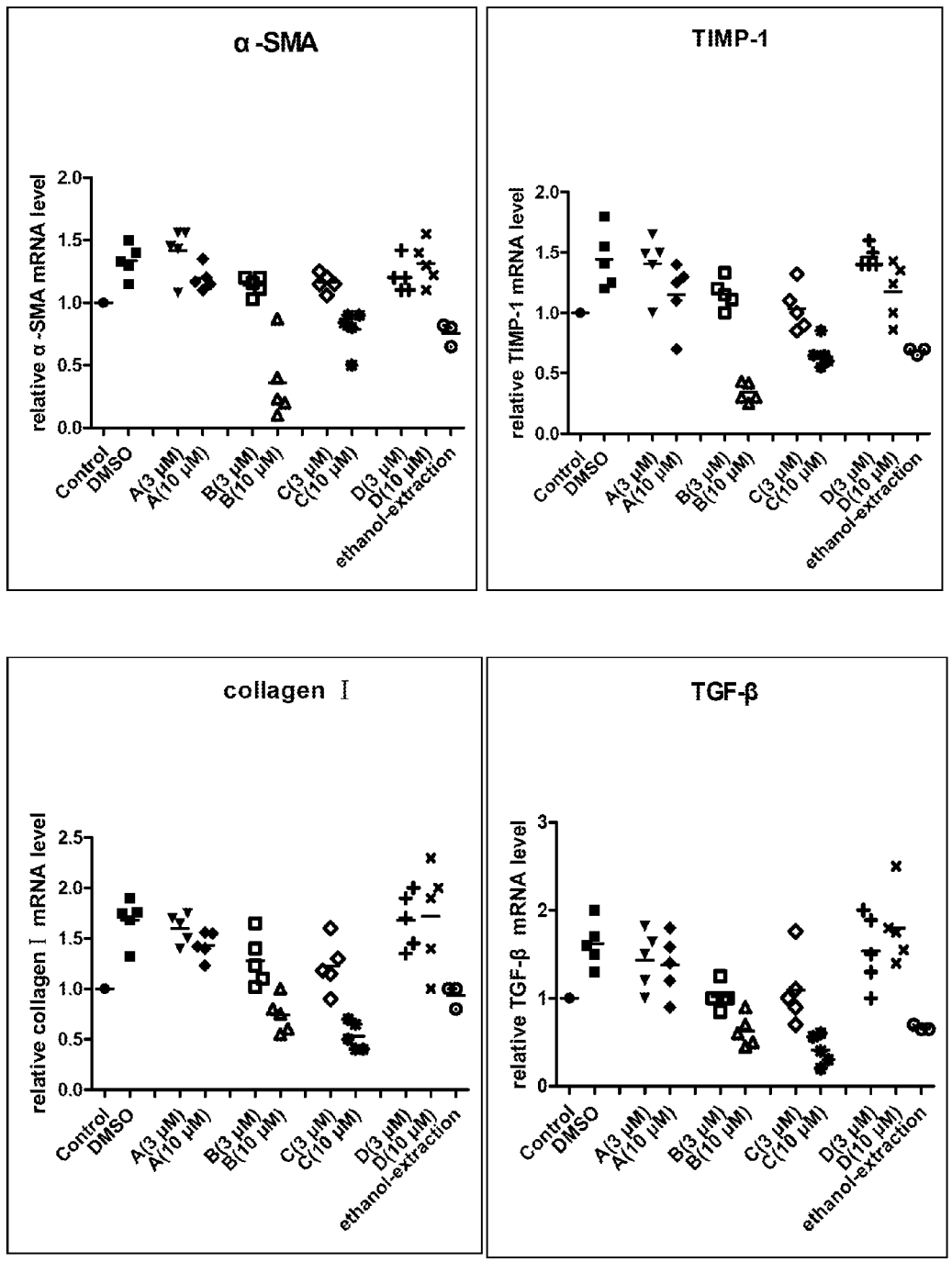
FIG. 20 shows all-4 profibrogenic genes expression was down-regulated significantly in primary HSC treated by compounds B, compound C and ACM ethanol extract.

Preventive Effects of Hepasim Compounds on Profibrogenic Gene Expression in Dermal Fibroblast All-4 profibrogenic gene expression was down-regulated significantly in dermal fibroblast treated by compound B, compound C and ACM ethanol extract, and the dose-dependent effect was noted also in compounds B and C (FIG. 20).

Conclusion

The summary of cellular study indicated that all compounds have significant protective effects on keratocyte damage from oxidative stress such as sun exposure. Compound B and C also exhibited an anti-fibrosis effect on dermal fibroblast. It means the potential for prevention of hypertropic scar formation. In the in vitro experiments of UV exposure, hepasim compounds showed the ability to decrease intracellular melanin accumulation, and seemed to be the candidate to further determine anti-melanogenesis experiment in vivo, and higher dosage should be considered.

Example 5

Extract from Mycelium of Antrodia Cinnamomea

Water Extract

Fermentated mycelium of *Antrodia cinnamomea* was added in 85° C. hot water (mycelium:water=1:5 by weight) and evenly stirred 4 hours. Then the reaction mixture was cooled to 30° C. and liquid was separated by using a separator. The liquid was concentrated by vacuum evaporation to obtain the ACM water extract.

Ethanol Extract

Fermentated mycelium of *Antrodia cinnamomea* was added in ethanol (mycelium:ethanol=1:5 by weight), heated to 60-65° C. and stirred. Then the reaction mixture was cooled to 40° C. and liquid was separated by using a separator. The liquid was concentrated by vacuum evaporation to obtain the ACM ethanol extract. In an exemplary embodiment, the respective percentage of hepasim compounds in the ACM ethanol extract was shown below:

Compound A: 13.13%;
Compound B: 0.52%;
Compound C: 20.8%;
Compound D: 9.47%;
Compound E: 5.85%.

The mycelium of *Antrodia cinnamomea* was previously prepared according to submerged liquid fermentation such as T. L. M. Stamford et al., Food Science "Protein enrichment of cashew wastes for animal feeds" from http://www.unu.edu/unupress/food/8F101e/8F101E0b.htm.

The ACM (mycelium of *Antrodia cinnamomea*) ethanol extract was also used in some of the assays described in previous experiments, and the data was shown in FIGS. 7-12, 19-20. All the methods were the same except that the hepasim compound is replaced by the ACM ethanol extract.

Example 6

Animal Model for Scar Formation

Animal Model

The rabbit ear model of hypertrophic scarring was established. In brief, 12 New Zealand white rabbits, weighing 2.5 to 3.0 kg, were prepared for wounding under sterile conditions. Four 1 cm full thickness circular wounds were created down to the cartilage on the ventral side of each ear using a 1 cm punch biopsy. The perichondrial membrane was then dissected off the cartilage using a surgical blade. The test agents including compound B, C and ACM ethanol extract were applied to the wounds of the experimental group (10 mL to each wound) every day in concentrations of 1% w/v for 14 days, while the control group received equal amounts of 1% w/v saline.

Collagen I and Collagen III Quantification

The quantification of collagen I and III used an ELISA Kit (R & D Systems Inc., Minneapolis, Minn., USA) according to the operation manual.

Western Blot

The scar tissues were lysed; then the protein samples were denatured and then separated on 10.6% polyacrylamide gels, and transferred to the polyvinylidene difluoride membrane. The membranes were incubated in TBS containing 5% nonfat milk and 0.05% Tween-20 for 1 h at room temperature and blotted with primary antibodies (dilution 1:300) at 4° C. overnight. The membranes were washed with TBST for 15 min the next day. Subsequently, the membranes were incubated with horseradish peroxidase-conjugated affinipure goat anti-rabbit antibody (dilution 1:3000) for 1 h at room temperature and washed with TBST for 21 min. The membranes were then detected using ECL. The western blot results were further analyzed with Quantity One software 4.1.1 (Bio-Rad, Hercules, Calif.)

Results

Compound B, C and Ethanol Extraction Alleviates the Scar Formation in the Rabbit Ear Model All wounds had adequate scar maturation and showed histologic evidence of scarring. The mean scar thickness (SEI) in the control group was 3.71±0.31, which was higher significantly than that of the compound B, C and ethanol extraction group with 1.93±0.51, 2.10±0.24 and 2.13±0.44 on days 14 respectively (P<0.05). The mean epidermal thickness (ETI) of the control group was 5.08±0.44 compared with 2.23±0.31, 3.10±0.14 and 3.35±0.24 for the compound B, C and ethanol extraction group (P<0.05). This represents a significant epidermal thickness reduction in wounds treated with compound B, C and ethanol extraction.

Histologically, the dermis layer of the control scars thickened significantly, and the boundary between the papillary and reticular layers of dermis was obscure; collagen fibers were dense, with derangements in collagen bundles. The number of cells also increased, while the basal layer of the epidermis in the scars treated with compound B, C and ethanol extraction for 14 day was flattened. The dermis layer was not significantly thickened, and collagen fibers were well arranged, with few cells.

Effect of Test Agents on Collagen I and Collagen III Synthesis

In order to evaluate the molecular effects of test agents on matrix production, protein density of collagen I and III, which constitute the bulk of the scar extracellular matrix (ECM), were measured. As expected, collagen I density was significantly decreased on day 14 (p<0.05), while collagen III density was insignificantly decreased on day 7 but significantly reduced on day 14 (p<0.05) in the compound B, C and ethanol extraction treated group.

Effect of Test Agents on α-SMA and TGF-β1 Expression

The persistent presence of myofibroblasts is a distinctive feature of hypertrophic scar (HTS) that contributes to the excessive matrix production. Western blot analysis showed that levels of α-SMA expression decreased in the compound B, C and ethanol extraction groups relative to the control group (p<0.05). Western blot analysis showed also that the level of TGF-β1 expression significantly decreased in the compound B, C and ethanol extraction group compared with the control groups on day 14 (p<0.05).

One skilled in the art readily appreciates that the present invention is well adapted to carry out the objects and obtain the ends and advantages mentioned, as well as those inherent therein. The compound, composition, extraction and mixture, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for whitening skin comprising: a step of applying a therapeutically effective amount of a composition to the skin of an individual in need of skin whitening, wherein the composition comprises a compound having the formula

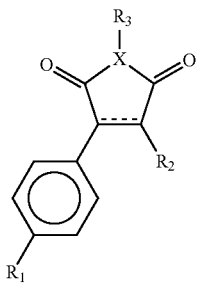

or its tautomeric forms, its stereoisomers, its polymorphs, its salts, or its solvates,
wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl;
$R_3$ is H, hydroxyl, $C_{1-10}$ alkyl, $C_{2-10}$ alkenyl or $C_{2-10}$ alkynyl;
----- denotes a single or double bond;
provided that
if X is O, $R_3$ is absent;
if ----- denotes a single bond, the compound has the formula:

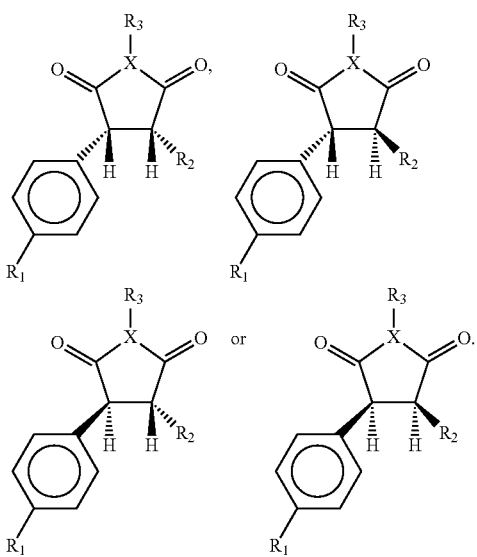

wherein the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione, or
3-isobutyl-4-[4-(3-methyl-2-butenyloxy)phenyl]-1H-pyrrol-1-ol-2,5-dione.

2. The method of claim 1, wherein the composition is a cosmetic or dermatologic preparation for external use.

3. The method of claim 1, wherein tyrosinase and thereby biosynthesis of melanin are inhibited.

4. A method for combating skin ageing comprising: a step of applying a therapeutically effective amount of a composition to the skin of an individual in need of combating skin aging, wherein the composition comprises a compound having the formula

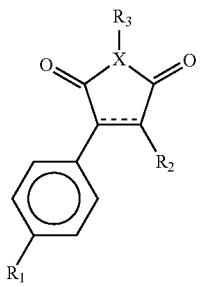

or its tautomeric forms, its stereoisomers, its polymorphs, its salts, or its solvates, wherein X is N or O;

R1 is H, hydroxyl, C1-10 alkyloxy, C2-10 alkenyloxy, or C2-10 alkynyloxy;

R2 is H, hydroxyl, C1-10 alkyl, C2-10 alkenyl or C2-10 alkynyl;

R3 is H, hydroxyl, C1-10 alkyl, C2-10 alkenyl or C2-10 alkynyl;

----- denotes a single or double bond;

provided that if X is O, R3 is absent;

if ----- denotes a single bond, the compound has the formula:

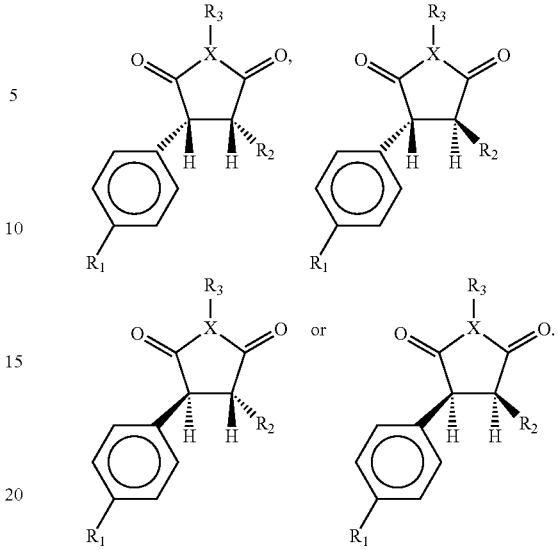

wherein the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione, or
3-isobutyl-4-[4-(3-methyl-2-butenyloxy)phenyl]-1H-pyrrol-1-ol-2,5-dione.

5. The method of claim 4, wherein the composition is a cosmetic or dermatologic preparation for external use.

6. The method of claim 4, wherein the skin ageing is caused by oxidative stress.

7. The method of claim 6, wherein the oxidative stress is induced by UV exposure.

* * * * *